United States Patent [19]
Yasuzawa et al.

[11] Patent Number: 4,952,576
[45] Date of Patent: Aug. 28, 1990

[54] UCY1003 DERIVATIVES

[75] Inventors: Toru Yasuzawa; Hiroshi Sano; Hirofumi Nakano, all of Tokyo; Shunji Ichikawa; Katsuichi Shuto, both of Shizuoka, all of Japan

[73] Assignee: Kyowa Hakko Kogyo Kabushiki Kaisha, Japan

[21] Appl. No.: 223,193

[22] Filed: Jul. 22, 1988

[30] Foreign Application Priority Data

Jul. 24, 1987 [JP] Japan ................. 62-184968

[51] Int. Cl.$^5$ .............. A61K 31/58; C07J 71/00
[52] U.S. Cl. .................. 514/172; 540/62; 540/76; 540/93
[58] Field of Search ............ 540/62, 76, 93; 514/172

[56] References Cited

U.S. PATENT DOCUMENTS

| | | | |
|---|---|---|---|
| 3,455,906 | 7/1969 | Marshall et al. | 540/76 |
| 3,579,499 | 5/1971 | Clarkson | 540/62 |
| 4,519,946 | 5/1985 | Teutsch et al. | 540/76 |

FOREIGN PATENT DOCUMENTS 0228700 12/1986 European Pat. Off.

OTHER PUBLICATIONS

Chemical Abstracts, vol. 108, No. 11, Mar. 14, 1988, pp. 369–370.

*Primary Examiner*—Joseph A. Lipovsky
*Attorney, Agent, or Firm*—Wolder, Gross & Bondell

[57] ABSTRACT

Compounds having analgesic activity which have the formula

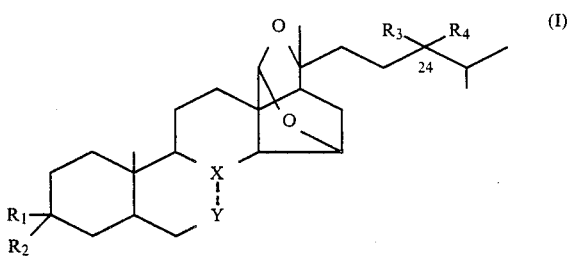

or

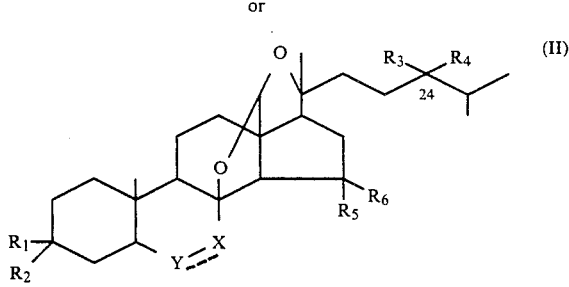

wherein $R_1$-$R_6$ represent hydrogen or a substituent and X and Y together represent inter alia as epoxyethylene, ethylene halohydrin, haloethylene or a —CH=CH— group.

9 Claims, No Drawings

UCY1003 DERIVATIVES

The present invention relates to UCY1003 derivatives which exhibit analgesic activity.

It is known that certain steroid-type compound such as, for example, triamcinolone, methylprednisolone and dexamethasone have analgesic activity [Igaku no Ayumi (Development of Medical Science) 139 (1), 41 (1986)]. It is also known that the steroide substance designated UCY1003 has analgesic activity (EP-A-228 700).

Additional and./or improved analgesic agents are always needed. We have now prepared new UCY1003 derivatives having a surprising level of analgesic activity.

The present invention provides new UCY1003 derivatives having analgesic activity and represented by the formula:

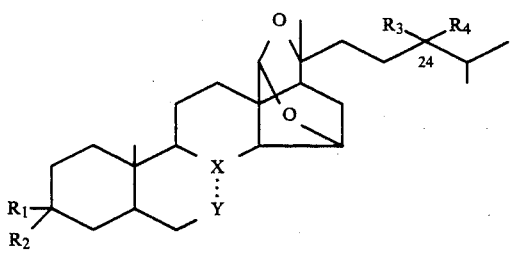

[wherein one of $R_1$ and $R_2$ represents hydrogen and the other represents OR (wherein R represents hydrogen or a $C_1$-$C_4$- alkanoyl group), or $R_1$ and $R_2$ in combination together represent a keto group; one of $R_3$ and $R_4$ represents hydrogen and the other represents methyl; or $R_3$ and $R_4$ in combination together represent $CH_2$: X and ...Y - are combined together and represent

(wherein Z represents hydrogen or halogen) or

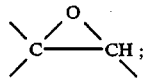

or X and ...Y - are not combined together and X represents C=O and Y represents COOH: provided that when $R_1$ represents ..H and $R_2$ represents - OH and when $R_3$ and $R_4$ in combination together represent $CH_2$, X ...Y are combined together and do not represent

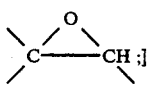

In another aspect, our invention provides UCY1003 derivatives represented by the formula (II): -

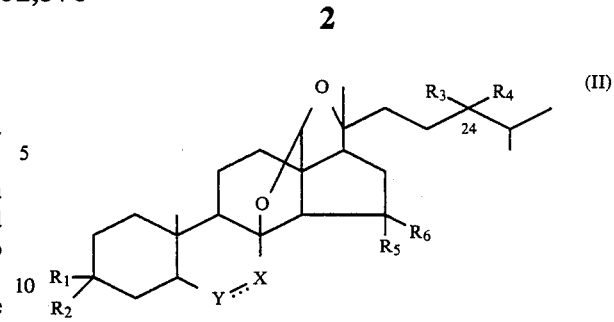

wherein one of $R_1$ and $R_2$ represents hydrogen and the other represents OR (wherein R represents hydrogen atom or a $C_1$-$C_4$-(alkanoyl group)
or $R_1$ and $R_2$ in combination together represent a keto group;

one of $R_3$ and $R_4$ represents hydrogen and the other represents methyl; or $R_3$ and $R_4$ in combination together represent $CH_2$;

$R_5$ and $R_6$ each represents hydrogen or hydroxyl or $R_5$ and $R_6$ in combination together represent a keto group: —X—Y represents —CHZ—$CH_2$—(wherein Z represents hydrogen or halogen) or —CH=CH—].

In the above formulae, examples of suitable $C_1$-$C_4$ alkanoyl groups include straight or branched alkanoyl such as formyl, acetyl and propionyl groups; suitable halogen atoms are exemplified by chlorine and bromine.

Compounds of superior analgesic activity include those wherein one of $R_1$ and $R_2$ represents hydroxy or acetyloxy; Z presently represents chlorine or bromine. Compound of particular interest include those wherein
one of $R_1$ and $R_2$ represents hydroxy or acetyloxyl;
one of $R_3$ and $R_4$ represents methyl
one of $R_5$ and $R_6$ represents hydroxy and the other represents hydrogen
and Z represents bromine.

For analgesic use, the compound may be formulated in conventional manner by admixing an effective amount with a pharmacologically acceptable carrier or excipient.

Suitable $C_1C_4$ alalkanoyl groups have already been described.

Step 1

Compound la may be obtained by the reaction of UCY1003 with a carboxylic acid anhydride or acyl halide in an aprotic organic solvent, in the presence of a base.

Suitable carboxylic acid anhydrides and acyl halides include, for example, anhydrides and acyl halides of acetic acid, propionic acid, lactic acid and isolactic acid. Such acid anhydrides and acyl halides may e.g. be used in a ratio of 5-20 moles per mole of UCY1003. Suitable aprotic organic solvents are exemplified by chloroform, dichloromethane, trichloroethane, benzene, toluene, acetone, ethyl acetate, trichloroethane, dioxane, tetrahydrofuran and dimethylformamide.

Suitable bases include tertiary amines and alkali metal carbonates, e.g. pyridine, quinoline, triethylamine, sodium carbonate and potassium carbonate. Especially good results may be obtained by the use of pyridine. An excess of pyridine may serve as the aprotic organic solvent.

The reaction may be effected at a temperature of −10° to 120° C., preferably 10 to 30° C. for a period of e.g. 0.5 to 20 hours preferably 3 to 8 hours.

The reaction product may be isolated by pouring

:on solution into water. The product so the react: isolated may have a sufficient purity for use or may, if desired, be purified further, for example, by column chromatoqraphy on silica gel or by recrystallization from an organic solvent.

Suitable organic solvents include, for example, chloroform, benzene, toluene, acetone, ethyl acetate, hexane, methanol, ethanol and ether, although the use of methanol or ethyl acetate is preferred.

Step 2

Compound 1b may be obtained by treating UCY1003 with an oxidizing agent derived from chromium (VI) oxide in an organic solvent.

Suitable oxidizing agents derived from chromium (VI) oxide are exemplified by chromium (VI) oxide-sulfuric acid (Jones reagent), chromium (VI) oxide-acetic acid, chromium (VI) oxide-pyridine complex (Collins reagent), pyridinium dichromate (PDC) reagent and pyridinium chlorochromate (PCC) reagent. the use of Jones reagent, PDC reagent or PCC reagent is preferred.

Preferably one uses from 3 to 5 moles of the oxidizing agent per mole of UCY1003.

Examples of suitable inert organic solvents include methylene dichloride, cis-1, 2-dichloroethylene, trans-1, 2-dichloroethylene, pyridine, chloroform, 1,2-dichloroethane, 1,1-dichloroethane, carbon tetrachloride, dimethyl sulfoxide and dimethylformamide. Especially good results may be obtained by using methylene dichloride.

The reaction may e.g. be effected at a temperature of from 0 to 40° C., preferably 10 to 25° C., for a period of e.g. 5 minutes to 24 hours, preferably 0.5 to 5 hours.

The purification in this step (and in the following steps) may be effected in a similar manner to that described in Step 1.

Step 3

Compound 1c may be prepared by catalytic hydrogenation of UCY1003 in an organic solvent.

Examples of suitable organic solvents include ethanol, methanol, tetrahydrofuran, ethyl acetate, dioxane, cyclohexane, acetic acid and dimethylformamide. Methanol is preferred. Suitable catalysts are e.g. based on nickel, platinum, rhodium or most preferably palladium.

The reaction may be effected at a temperature of e.g. −0° to 60° C., preferably 20 to 30° C. for a period of e.g. 0.5 to 10 hours, preferably 0.5 to 2 hours.

The product is usually a mixture of isomers having different absolute configurations at the 24th position in a molar ratio of from 1:4 to 4:1.

Step 4

Compound 1d may be obtained by treating UCY1003 with an oxidizing agent derived from chromium (VI) oxide in an inert organic solvent.

Examples of inert organic solvents include methylene dichloride, cis-1, 2-dichloroethylene, trans-1, 2-dichloroethylene, pyridine, chloroform, 1, 2-dichloroethane, 1, 1-dichloroethane, carbon tetrachloride, dimethylsulfoxide and dimethylformamide. Especially good results may be obtained by the use of methylene dichloride. Suitable oxidizing agents are exemplified by chromium (VI) oxide-sulfuric acid (Jones reagent).

One may use preferably from 3 to 5 moles of the oxidizing agent per mole of UCY1003.

The reaction may he effected at a temperature of e.g. 10 to 40° C., preferably 20 to 30° C., for a period of e.g. 0.5 to 24 hours, preferably 0.5 to 5 hours.

Step 5

Compound 1e (wherein Z=halogen) may be prepared by the raction of UCY1003 with a hydrohalic acid, e.g. hydrochloric or hydrobromic acid, in an organic solvent.

Examples of suitable organic solvents include ethanol, methanol, methylene dichloride, chloroform, ethyl acetate, acetone, tetrahydrofuran, dioxane, dimethylformamide and dimethylsulfoxide. Especially good results may be obtained by the use of tetrahydrofuran.

The reaction may e.g. be effected at a temperature of −20° to 50° C., preferably 0 to 30° C. for a period of 5 minutes to 5 hours, preferably from 10 minutes to one hour.

Compound 1e (wherein Z=H) may be prepared by treating UCY1003 with a reducing agent in an inert organic solvent.

Suitable solvents inert in this reaction are exemplified by ether, benzene, toluene, xylene, hexane, tetrahydrofuran, 1,2-dimethoxyethane and diglyme. The use of tetrahydrofuran is preferred.

Suitable reducing agents are exemplified by lithium aluminium hydride and its alkoxy derivatives containing, for example, -methoxy, ethoxy, tert-butoxy or methoxyethoxy. We prefer to use lithium aluminium hydride.

The reaction may e.g. be effected at a temperature of from 0 to 100° C., preferably 40 to 70° C. for a period of from 1 minute to 10 hours, preferably from 10 minutes to 3 hours.

Step 6

Compound IIa may be obtained by allowing Compound Ia to stand in an organic solvent e.g. at a temperature of from 0 to 100° C., preferably 10 to 70° C. for a period of from 30 minutes to 3 days, preferably from 1 to 20 hours. If desired, the reaction may be accelerated by an catalytic acid, e.g. formic, acetic, para-toluenesulfonic, trifluoroacetic, hydrochloric, hydrobromic, sulfuric, nitric or phosphoric acid. The use of hydrochloric acid is preferred.

Suitable organic solvents include chloroform, dichloromethane, dichloroethane, benzene, toluene, aceton, ethyl acetate, dioxane, tetrahydrofuran, methanol and ethanol. The use of tetrahydrofuran is preferred.

Step 7

It is also possible to obtain Compound IIa in a similar manner to that described in Step 6 except the use of UCY1003 instead of Compound 1e.

Step 8

Compound IIc may be obtained by heating Compound IIa in an organic solvent containing a base e.g. at a temperature of from 20 to 200° C., preferably from 50 to 80° C. for a period of from 30 minutes to 20 hours, preferably from 1 to 10 hours.

Suitable organic solvents include methanol, ethanol, acetone, tetrahydrofuran, dioxane, 2-methoxyethanol, ethylene glycol, dimethylformamide and dimethylsulfoxide. These organic solvents may be used in anhydrous or aqueous form. We prefer to use methanol.

Suitable bases include sodium hydroxide, potassium hydroxide, lithium hydroxide, lithium carbonate, calcium carbonate, pyridine, collidine, sodium ethoxide, potassium tert-butoxide, 1.8-diazabicyclo (7,4,0) -7- undecene, 1,5-diazabicyclo [4.3.0]non-5-ene, and hexamethylphosphorotriamide. The use of potassium hydroxide is preferred.

Step 9

Compound IId may be obtained in a similar manner to that described in Step 1, starting from Compound IIa instead of UCY1003.

Step 10

Compound IIb may be obtained by treating Compound IId with an oxidizing agent derived from chromium (VI) oxide in an inert organic solvent. Suitable oxidizing agents and solvents are those defined for Step 2 above.

Preferably one may use from 3 to 5 moles of the oxidizing agent per mole of Compound IId.

The reaction may be effected e.g. at a temperature of from 0 to 80° C., preferably from 10 to 25° C. for a period of from 10 minutes to 20 hours, preferably from 0.5 to 5 hours.

Step 11

Compound IIe may be obtained from Compound Ic under the conditions described in Step 7.

The resultant product is usually a mixture of isomers having different absolute configurations at the 24th position, whose ratio corresponds to the isomer mixture in Compound Ic.

Step 12

Compound IIf may be obtained in a similar manner to that described in Step 1 except for the use of Compound IIe as starting material instead of UCY1003.

The product is usually a mixture of substances having different absolute configurations at the 24th position, thus corresponding to the isomer mixture in Compound IIe.

The following Table 1 indicates preferred examples of the compounds of the present invention and intermediate therefore wherein Compounds 1-16 correspond respectively to the compounds obtained in Examples 1-16 described hereinafter.

TABLE 1

| Compound No. | Formula |
| --- | --- |
| 1 | |
| 2 | |
| 3 | |
| 4 | |

TABLE 1-continued
| Compound No. | Formula |
|---|---|
| 5 | 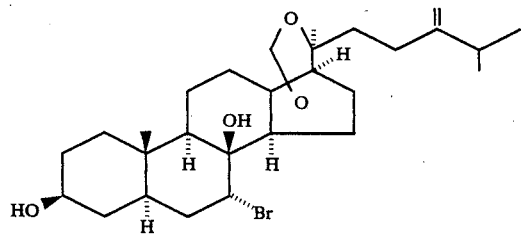 |
| 6 | 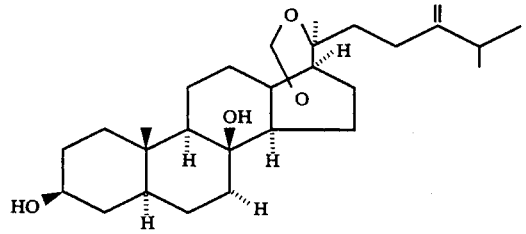 |
| 7 | 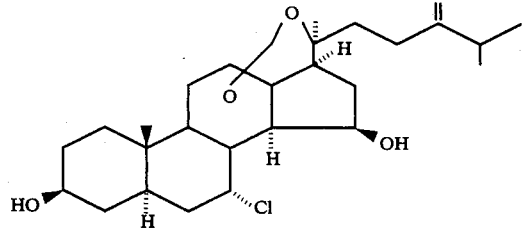 |
| 8 | 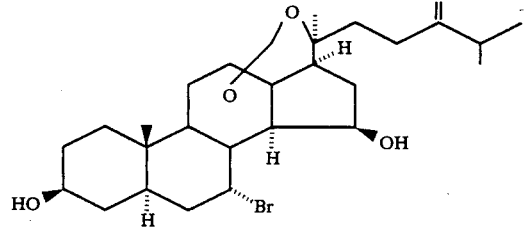 |
| 9 | 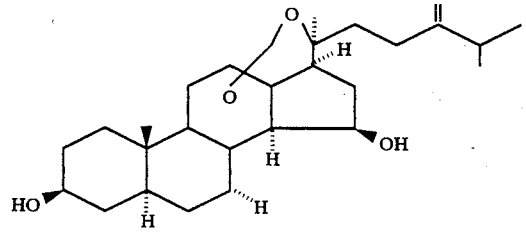 |
| 10 | 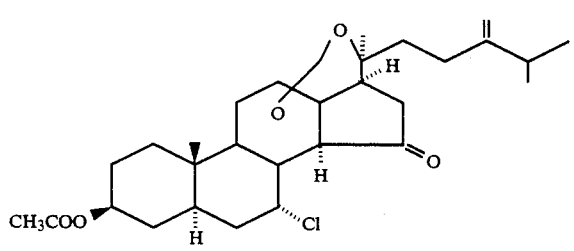 |

TABLE 1-continued

| Compound No. | Formula |
|---|---|
| 11 | |
| 12 | |
| 13 | |
| 14 | |
| 15 | |
| 16 | |

The physico-chemical characteristics of Compounds 1–16 are shown in the following Tables 2 and 3.

Table 2 indicates the molecular formula, Rf by TLC, melting point and specific rotation of each compound. The following footnotes apply to Table 2:

(1) the molecular formula was determined from the elemental analysis or high resolution mass spectrometry:

(2) the Rf was determined by TLC using a solvent system of hexane/ethyl acetate (1:1 v/v):

(3) Rf was determined by TLC using a solvent system of chloroform/methanol/acetic acid (10:1:0.1 v/v);

(4) Rf was determined by TLC using a solvent system of hexane/ethyl acetate (5:1 v/v); and (5) all Rf values were determined by using TLC plate Kieselgel 60 F254 (commercial product of Merck AG., West Germany).

The physico-chemical characteristics of Compounds 1–16 are shown in the following Tables 2 and 3.

TABLE 2

| Compound No. | Molecular formula[1] | Rf by TLC[2,5] | M.P. (°C.) | $[\alpha]_D^{22}$ (CHCl$_3$) |
|---|---|---|---|---|
| 1 | C$_{30}$H$_{44}$O$_5$ | 0.61 | 238–239 | −62.5° |
| 2 | C$_{28}$H$_{40}$O$_4$ | 0.30 | 226–227 | −29.3° |
| 3 | C$_{28}$H$_{44}$O$_4$ | 0.13 | 234–235 | −55.3° |
| 4 | C$_{28}$H$_{40}$O$_6$ | 0.62[3] | 170–171 | −5.0° |
| 5 | C$_{28}$H$_{43}$O$_4$Br | 0.55 | 161–162 | −57.9° |
| 6 | C$_{28}$H$_{44}$O$_4$ | 0.45 | 206–207 | −25.6° |
| 7 | C$_{28}$H$_{43}$O$_4$Cl | 0.54 | 169–170 | −43.7° |
| 8 | C$_{28}$H$_{43}$O$_4$Br | 0.50 | 211–212 | −82.0° |
| 9 | C$_{28}$H$_{44}$O$_4$ | 0.33 | 171–172 | −9.3° |
| 10 | C$_{30}$H$_{43}$O$_5$Cl | 0.80 | 216–217 | −53.4° |
| 11 | C$_{28}$H$_{42}$O$_4$ | 0.33 | 177–178 | −56.7° |
| 12 | C$_{30}$H$_{45}$O$_5$Br | 0.43[4] | 161–162 | −80.1° |
| 13 | C$_{28}$H$_{45}$O$_4$Br | 0.53 | 219–220 | −91.1° |
| 14 | C$_{30}$H$_{47}$O$_5$Br | 0.45[4] | 179–180 | −64.7° |
| 15 | C$_{28}$H$_{43}$O$_4$Cl | 0.61 | 171–172 | −50.8° |
| 16 | C$_{30}$H$_{44}$O$_5$ | 0.79 | 210–211 | +18.9° |

TABLE 3

Table 3 indicates carbon-NMR of each compound in deutrochloroform

| 1 | 2 | 3 | | 4 | 5 | 6 | 7 | 8 |
|---|---|---|---|---|---|---|---|---|
| 170.7 | 210.6 | 106.6 | | 210.5 | 155.4 | 155.6 | 155.3 | 155.1 |
| 155.6 | 155.5 | 85.6, | 85.5 | 205.5 | 106.7 | 107.1 | 109.2 | 109.3 |
| 106.7 | 106.6 | 72.8 | | 176.7 | 106.5 | 106.5 | 106.8 | 106.8 |
| 106.4 | 106.4 | 71.0 | | 155.2 | 85.3 | 85.0 | 93.9 | 93.7 |
| 85.2 | 85.2 | 60.2 | | 106.5 | 74.7 | 74.3 | 88.7 | 88.5 |
| 73.1 | 72.8 | 58.6 | | 105.1 | 74.1 | 71.9 | 73.5 | 73.5 |
| 72.8 | 60.3 | 56.5 | | 86.1 | 71.0 | 71.4 | 70.8 | 70.6 |
| 60.1 | 58.6 | 54.6 | | 72.4 | 60.9 | 61.6 | 63.5(2) | 64.4 |
| 58.7 | 56.1 | 49.0, | 48.9 | 64.3 | 58.0 | 57.3 | | 63.8 |
| 56.4 | 54.3 | 48.7 | | 63.5 | 57.7 | 53.8 | 60.6 | 54.7 |
| 54.5 | 49.0 | 39.8 | | 55.2 | 49.2 | 49.2 | 52.6 | 52.5 |
| 49.1 | 48.0 | 39.4, | 39.2 | 49.2 | 47.2 | 45.4 | 48.2 | 48.0 |
| 48.6 | 43.9 | 39.2, | 39.1 | 42.6 | 39.5 | 40.3 | 38.1 | 37.9(2) |
| 39.6(2) | 42.0 | 38.1 | | 39.5 | 38.1 | 39.6 | 37.5 | |
| | 39.6 | 37.4 | | 39.1 | 37.6 | 37.8 | 37.0 | 37.4 |
| 37.8 | 39.4 | 35.5, | 35.4 | 37.2 | 36.8 | 37.5 | 36.9 | 36.8(2) |
| 35.4 | 37.3 | 33.9 | | 36.5 | 36.0 | 35.8 | 36.7 | |
| 33.9(2) | 35.3 | 31.9, | 31.8 | 35.0 | 34.9 | 35.2 | 36.5 | 36.6 |
| | 34.0 | 30.8 | | 34.0 | 34.0 | 34.0 | 33.9 | 34.5 |
| 33.3 | 33.9 | 29.2, | 28.9 | 33.8 | 33.7 | 31.0 | 33.7 | 33.8 |
| 29.5 | 29.4 | 28.6 | | 30.3 | 30.7 | 29.5 | 32.4 | 32.3 |
| 28.4 | 28.9 | 28.4 | | 29.2 | 29.4 | 28.8 | 30.5 | 30.4 |
| 28.3 | 28.2 | 27.4 | | 27.5 | 28.1 | 24.9 | 28.3 | 28.2 |
| 27.4 | 27.4 | 21.7 | | 27.1 | 27.2 | 27.2 | 24.9 | 24.8 |
| 26.7 | 21.9(2) | 20.4, | 20.2 | 25.4 | 21.9(2) | 21.9(2) | 21.9(2) | 21.8(2) |
| 21.9(2) | | 18.2, | 17.7 | 21.8(2) | | | | |
| | 21.8 | 15.5, | 15.3 | | 19.0 | 18.9 | 20.6 | 20.5 |
| 21.7 | 12.0 | 12.8 | | 16.7 | 12.7 | 12.5 | 12.1 | 12.2 |
| 21.4 | | | | | | | | |
| 12.7 | | | | | | | | |

| 9 | 10 | 11 | 12 | 13 | | 14 | 15 | 16 |
|---|---|---|---|---|---|---|---|---|
| 155.5 | 207.3 | 155.4 | 170.5 | 109.4 | | 170.6 | 155.4 | 210.2 |
| 108.3 | 170.6 | 135.0 | 155.3 | 93.7 | | 109.4 | 106.9 | 170.7 |
| 106.7 | 155.0 | 126.4 | 109.4 | 89.2 | | 93.7 | 106.6 | 155.2 |
| 91.8 | 108.8 | 107.7 | 106.9 | 73.7 | | 89.2 | 85.3 | 108.0 |
| 88.1 | 106.7 | 106.7 | 93.8 | 70.9 | | 73.7 | 75.0 | 106.6 |
| 73.1 | 92.3 | 89.2 | 88.7 | 64.6 | | 73.1 | 74.2 | 90.7 |
| 71.1 | 88.3 | 88.2 | 73.7 | 63.9 | | 64.6 | 71.0 | 87.5 |
| 64.4 | 73.0 | 72.9 | 73.0 | 54.9 | | 63.9 | 65.3 | 73.3 |
| 64.1 | 60.7 | 71.4 | 64.5 | 52.7, | 52.5 | 54.4 | 57.6 | 62.8 |
| 54.7 | 59.5 | 65.5 | 63.9 | 48.2 | | 52.7, 52.5 | 56.3 | 60.2 |
| 52.5 | 59.3 | 64.4 | 54.3 | 39.2, | 39.0 | 48.0 | 49.2 | 54.5 |
| 44.8 | 47.2 | 55.1 | 52.8 | 38.1(2) | | 39.2, 39.0 | 47.3 | 45.4 |
| 38.6 | 45.0 | 52.3 | 48.0 | | | 38.1 | 39.5 | 44.5 |
| 38.0 | 41.0 | 45.2 | 38.0 | 37.6 | | 37.9 | 37.6 | 41.4 |
| 37.8 | 37.1 | 38.5 | 37.9 | 37.0 | | 37.3 | 36.9 | 37.5 |
| 36.9 | 36.9(2) | 36.9 | 37.2 | 36.8 | | 36.7 | 36.8 | 36.5 |
| 36.3 | | 36.2 | 37.0 | 36.3, | 36.1 | 36.3, 36.1 | 35.9 | 36.3 |
| 33.9 | 36.3 | 35.1 | 36.7 | 34.6 | | 34.5 | 34.9 | 34.0 |
| 32.7 | 34.1 | 34.5 | 34.4 | 32.4 | | 32.9 | 34.0 | 33.7 |
| 31.8 | 33.2 | 33.9 | 34.0 | 32.0 | | 32.4 | 33.0 | 32.8 |
| 30.8 | 32.8 | 32.6 | 32.9 | 30.6 | | 32.0 | 30.8 | 31.7 |
| 28.4 | 32.5 | 30.7 | 32.4 | 28.1, | 27.8 | 28.0, 27.8 | 29.4 | 28.3 |
| 25.5 | 28.2 | 28.3 | 28.4 | 24.9 | | 26.7 | 28.2 | 26.7 |

TABLE 3-continued

Table 3 indicates carbon-NMR of each compound in deutrochloroform

| 24.9    | 26.6    | 24.7    | 26.6    | 20.7       |      | 24.9        |       | 27.2    | 25.1  |
| 21.9(2) | 24.3    | 21.9(2) | 24.9    | 20.4,      | 20.3 | 21.4        |       | 21.9(2) | 24.2  |
|         | 21.9(2) |         | 21.9(2) | 18.2,      | 17.9 | 20.6        |       | 18.9    | 21.94 |
| 21.0    |         | 21.1    |         | 15.4       |      | 20.35,      | 20.26 | 12.6    | 21.89 |
| 12.1    | 21.4    | 11.1    | 21.4    | 12.4       |      | 18.2, 17.9  |       |         | 21.4  |
|         | 20.5    |         | 20.6    |            |      | 15.4        |       |         | 20.9  |
|         | 11.9    |         | 12.2    |            |      | 12.3        |       |         | 12.0  |

Ppm was determined by using tetramethylsilane as the internal standard.

Acute toxicities and analgesic activities of the compounds of the present invention are as follows:

1. Acute toxicity:

3 mice of ddy strain were used as test animals. After intraperitioneal administration of test compounds, the animals were observed for 7 days to note the death ratio.

It was found that zero mortality resulted from administration of the compounds at a dose of 300 mg/kg.

2. Analgesic effect:

As test animals, female mice of ddy strain (body weight 20±1 g; each group consisting of 4 mice) were used. Each test compound was administered intraperitioneally. 60 minutes later, 0.7 % acetic acid solution (0.2 ml) was intraperitioneally administered and the number of writhing movements made within a period of 10 to 15 minutes after administration was noted. Where the number of writhing movements decreased by more than 70% relative to the control (untreated) animals, it was concluded that the analgesic effect was positive.

The minimum effective doses (MED) thus obtained are shown in Table 4.

TABLE 4

| Compound No. | MED (mg/kg) |
|---|---|
| 1 | 10 |
| 2 | 10 |
| 3 | 5 |
| 4 | ≦100 |
| 5 | 25 |
| 6 | 10 |
| 7 | 100 |
| 8 | 2.5 |
| 9 | 25 |
| 10 | 10 |
| 11 | 25 |
| 12 | 5 |
| 13 | 0.25 |
| 14 | 1 |
| UCY 1003 | 50 |

The compounds of the present invention may be prepared as indicated below:

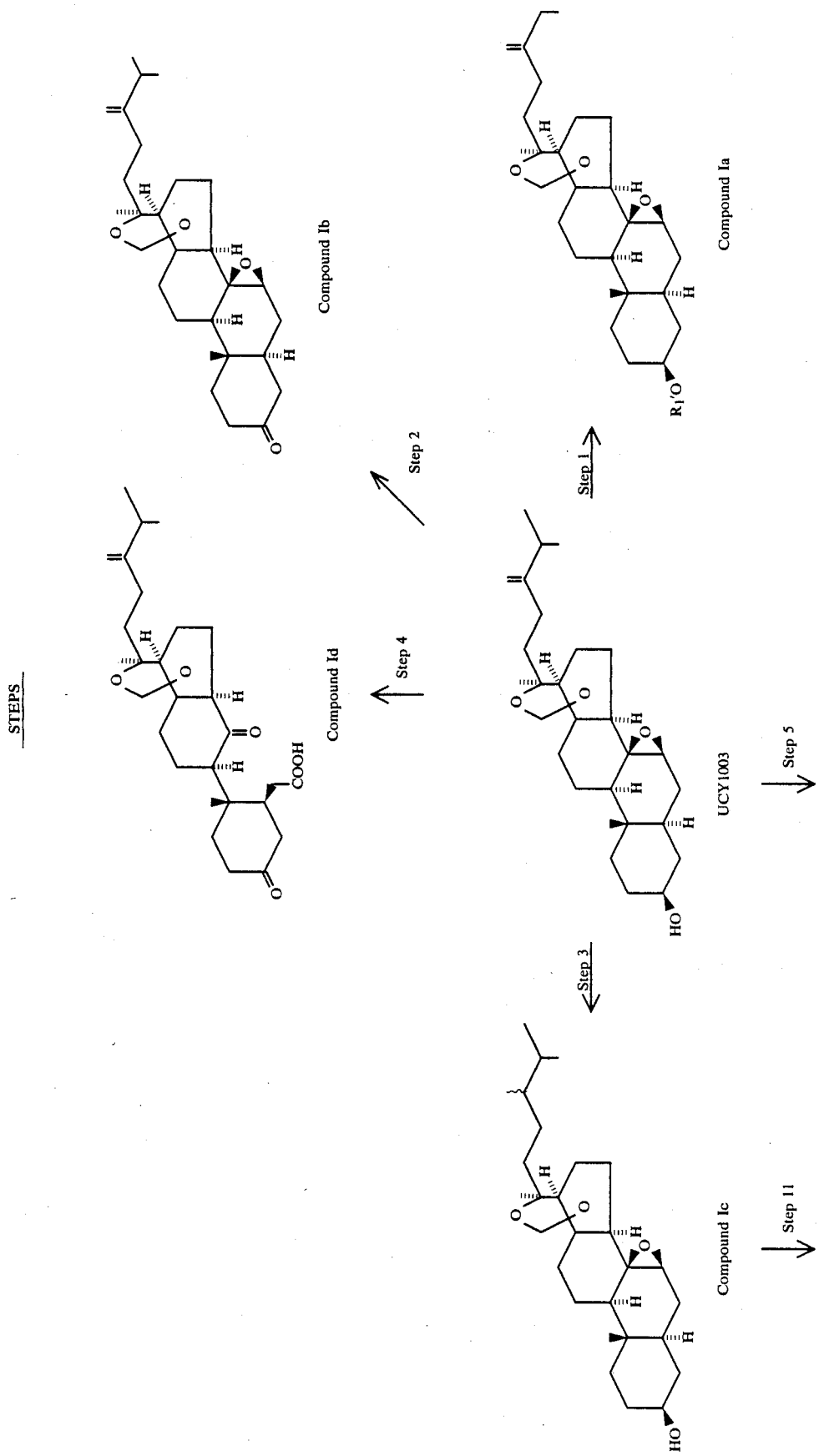

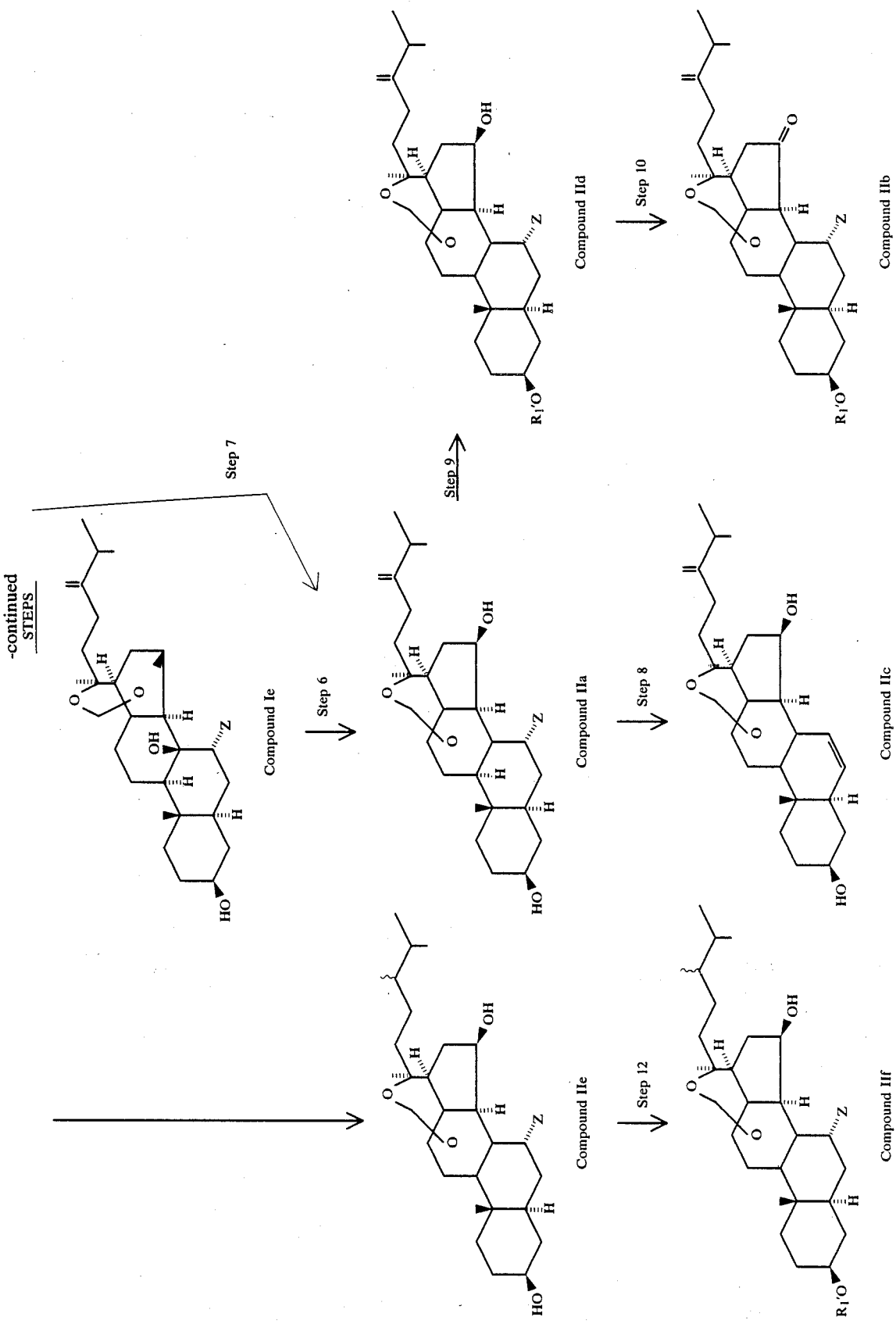

The following non-limiting Examples are given for illustration only.

UCY1003 used in the following Examples was obtained by the method of Example 1 of EP-A-228, 700.

EXAMPLE 1

UCY1003 (590 mg) was dissolved in pyridine (5 ml), and acetic anhydride (2 ml) was added thereto. After allowing the mixture to stand at room temperature for 5 hours, water (20 ml) was added. The solution was allowed to stand at room temperature for 30 minutes and then filtered to collect the precipitate. The precipitate was washed with water (100 ml) and dried at 80° C. for 3 hours to obtain Compound 1 (620 mg) as a colourless powder with a yield of 96%.

EXAMPLE 2

UCY1003 (802 mg) was dissolved in methylene chloride (20 ml). Pyridinium chlorochromate (PCC) reagent (1.61 g) was added to the solution, followed by stirring at room temperature for 2 hours. The reaction mixture was distributed between ethyl acetate (100 ml) and saturated aqueous sodium bicarbonate (100 ml). Then the aqueous layer was extracted twice with ethyl acetate (each 100 ml). The extracts were combined with the ethyl acetate layer. The combined organic fraction was washed with saturated sodium chloride solution (150 ml), dried over magnesium sulfate, and the solvent removed from by evaporation under reduced pressure to give a colourless powder. The powder was purified by silica gel column chromatography using a solvent system of hexane/ethyl acetate (1:2 v/v) to obtain Compound 2 (399 mg) as a colourless powder with a yield of 50%.

EXAMPLE 3

Palladium-carbon catalyst containing 10% palladium (450 mg) was stirred in methanol (30 ml) for 30 minutes under a hydrogen stream (1 atm). UCY1003 (620 mg), dissolved in methanol (20 ml), was added and the solution was stirred for 2 hours under the hydrogen stream. The reaction solution was filtered, the catalyst was washed with hot methanol (30 ml), and the combined filtrate and washing solution was evaporated under reduced pressure to give a colourless powder. The powder was purified by silica gel chromatography in chloroform/methanol (10:1 v/v) to obtain Compound 3 (440 mg) as a colourless powder, yield 71%.

EXAMPLE 4

UCY1003 (60 mg) was dissolved in acetone (5 ml). To this solution was added Jones reagent [0.2 ml; prepared from chromium trioxide (13.4 q), concentrated sulfuric acid (12 ml) and acetone (46 ml)]. the solution was stirred at room temperature for one hour and concetrated, then the mixture was distributed between ethyl acetate (30 ml) and water (30 ml). The water layer was extracted twice with ethyl acetate (each 30 ml) and the extracts were combined with the ethyl acetate layer. The combined organic fraction was washed with saturated sodium chloride solution and dried over magnesium sulfate. The residue was purified on silica gel column chromatography in chloroform/ methanol/acetic acid (30:1:0.1 v/v) to obtain Compound 4 (33 mg) as a colourless powder with a yield of 52%.

EXAMPLE 5

UCY1003 (1.39 g) was dissolved in tetrahydrofuran (25 ml) and 2N hydrobromic acid solution (1.5 ml) was added. The mixture was stirred at room temperature for 20 minutes. The reaction solution was neutralized with saturated sodium bicarbonate solution, followed by removal of the solvent under reduced pressure. The residue was distributed between ethyl acetate (100 ml) and water (100 ml). The water layer was extracted twice with ethyl acetate (each 100 ml) an the extracts were combined with the ethyl acetate layer. The combined organic fraction was washed with saturated sodium chloride solution, dried over magnesium sulfate and the residue purified by silica gel column chromatography in hexane/ethyl acetate (2:1 v/v) to obtain Compound 5 (1.41 g) as a colourless powder with a yield of 86%.

EXAMPLE 6

UCY1003 (1.23 g) was dissolved in anhydrous tetrahydrofuran (50 ml), followed by addition of lithium aluminium hydride (250 mg). The mixture was refluxed for 30 minutes and allowed to cool. Ethyl acetate (5 ml), methanol (5 ml) and water (1 ml) were in turn added to the reaction solution, followed by stirring for 10 minutes. The solvent was removed from the solution by evaporation under reduced pressure to give a residue. The residue was then distributed between 0,1N hydrochloric acid (100 ml) and ethyl acetate (100 ml). The aqueous layer was extracted twice with ethyl acetate (each 100 ml) and the extracts were combined with the ethyl acetate layer. The combined organic phase was washed with saturated sodium bicarbonate solution (100 ml) and saturated sodium chloride solution (100 ml) and then dried over magnesium sulfate. The solvent was removed by evaporation under reduced pressure to obtain Compound 6 (1.21 g) as a colourless powder with a yield of 99%.

EXAMPLE 7

UCY1003 (302 mg) was dissolved in tetrahydrofuran (7 ml). 2N hydrochloric acid (0.5 ml) was added to the mixture, followed by stirring at room temperature for one hour. The reaction solution was then neutralized with saturated sodium bicarbonate solution. The reaction solution was evaporated under reduced pressure to remove the solvent and the residue was distributed between chloroform (50 ml) and water (50 ml). The aqueous layer was extracted twice with chloroform (each 50 ml), and the extracts were combined with the chloroform layer. The combined organic phase was washed with saturated sodium chloride solution and dried over magnesium sulfate. The resultant solution was evaporated under reduced pressure to remove the solvent. The residue was purified by silica gel column chromatogrpahy in hexane/ethyl acetate (2:1 v/v) to obtan Compound 7 (235 mg) as a colourless powder with a yield of 72%.

EXAMPLE 8

UCY1003 (750 mg) was dissolved in tetrahydrofuran (25 ml), to which was then added 2N hydrobromic acid (1.5 ml). The mixture was Stirred at a temperature of 50° C. for 3 hours. The reaction solution was neutralized with saturated aqueous sodium bicarbonate and the solution was evaporated under reduced pressure to remove the solvent. Then the residue was distributed between ethyl acetate (100 ml) and water (100 ml). The aqueous layer was extracted twice with ethyl acetate (each 100 ml) and the extracts were combined with the ethyl acetate layer. The combined organic phase was washed with saturated sodium chloride solution and dried over magnesium sulfate. After removal of the solvent by evaporation under reduced pressure, the residue was purified by silica gel column chromatography in hexane/ethyl acetate (2;1 v/v) to obtain Compound 8 (620 mg) as a colourless powder with a yield of 70%.

EXAMPLE 9

Compound 6 (613 mg) was dissolved in tetrahydrofuran (50 ml) and 2N hydrochloric acid (2 ml) was added and the mixture was refluxed for 2 hours. The reaction solution was neutralized with saturated aqeuous sodium bicarbonate, the solvent was removed by evaporation under reduced pressure, and the residue was distributed between chloroform (50 ml) and water (50 ml). The aqueous layer was extracted twice with chloroform (each 50 ml). The extracts were combined with the chloroform layer and the combined organic phase was washed with saturated sodium bicarbonate solution (50 ml) and saturated sodium chloride solution (50 ml) and dried over magnesium sulfate.

After removal of the solvent by evaporation under reduced pressure, the residue was purified by silica gel column chromatography in hexane/ethyl acetate (1:1 v/v) to obtain Compound 9 (415 mg) as a colourless powder with a yield of 71%.

EXAMPLE 10

Compound 7 (6 mg) was dissolved in acetic anhydride (0.5 ml) and pyridine (1 ml) and allowed to stand at room temperature for one hour. After addition of water (0.5 ml), the mixture was allowed to stand for 30 minutes. The solvent was removed from the reaction solution by evaporation under redued pressure. The residue was dissolved in methylene chloride (1 ml). After addition of pyridinium chlorochromate (PCC) reagent (30 mg), the reaction solution was stirred at room temperature for 15 hours. The reaction mixture was distributed between ethyl acetate (30 ml) and water (30 ml). The water layer was extracted twice with ethyl acetate (each 30 ml). The extracts were combined with the ethyl acetate layer. After washing with saturated sodium chloride solution (30 ml), the combined organic phase was dried over magnesium sulfate.

After removal of the solvent by evaporation under reduced pressure, the residue was purified by silica gel column chromatography in hexane/ethyl acetate (5:1 v/v) to obtain Compound 10 (2.5 mg) as a colourless powder with a yield of 34%.

EXAMPLE 11

Compound 8 (275 mg) was dissolved in methanol (30 ml) and potassium hydroxide (5 g) was added to the solution. The mixture was refluxed for 5 hours. After the reaction mixture was concentrated, the concentrate was distributed between ethyl acetate (50 ml) and water (50 ml). The aqueous layer was extracted twice with ethyl acetate (each 30 ml). The extracts were combined with the ethyl acetate layer. The combined organic phase was washed with saturated sodium chloride solution and dried over magnesium sulfate. The residue was purified by silica gel column chromatography in hexane/ ethyl acetate (2:1 v/v) to obtain Compound 11 (215 mg) as a colourless powder with a yield of 93%.

EXAMPLE 12

Compound 8 (607 mg) was dissolved in pyridine (10 ml) and acetic anhydride (3 ml) was added to the solution. The mixture was allowed to stand at room temperature for 5 hours. After addition of water (5 ml), the mixture was allowed to stand at room temperature for 30 minutes. The reaction solution was concentrated and distributed between ethyl acetate (150 ml) and aqueous sodium bicarbonate (150 ml). The aqueous layer was extracted twice with ethyl acetate (each 150 ml). The extracts were combined with the ethyl acetate layer. The combined organic phase was washed with saturated sodium chloride solution and dried over magnesium sulfate. The residue was purified by silica gel column chromatography in hexane/ ethyl acetate (2:1 v/v) to obtain Compound 12 (590 mg) as a colourless powder with a yield of 90%.

EXAMPLE 13

Compound 3 (1.181 g) was dissolved in tetrahydrofuran (75 ml) and then 2N hydrobromic acid (1 ml) was added to the solution. The mixture was stirred at room temperature for 45 minutes. The reaction solution was neutralized with a saturated solution of sodium bicarbonate. The solvent was removed from the reaction solution by evaporation under reduced pressure. Ethyl acetate (150 ml) and water (150 ml) were used to distribute the residue. The aqueous layer was extracted twice with ethyl acetate (each 150 ml). The extract was combined with the ethyl acetate layer. The combined organic phase was washed with saturated sodium chloride solution and dried over magnesium sulfate. After removal of the solvent from the reaction solution by evaporation under reduced pressure, the residue (1.250 g) was dissolved in chloroform (30 ml). After addition of para-toluenesulfonic acid (200 mg), the solution was allowed to stand at room termperature for 4 hours. Chloroform (150 ml) and aqueous sodium bicarbonate (150 ml) were used to distribute the reaction solution.

The water layer was extracted twice with chloroform (each 150 ml). The extracts were combined with the chloroform layer. The combined organic phase was washed with saturated solution of sodium chloride and dried over magnesium sulfate. After removal of the solvent by evaporation under reduced pressure, residue was purified by silica gel column chromatography in hexane/ethyl acetate (3:1 v/v) to obtain Compound 13 (1.008 g) as a colourless powder with a yield of 74%.

EXAMPLE 14

Compound 13 (489 mg) was dissolved in pyridine (10 ml). Acetic anhydride (2.5 ml) was added to the solution. After allowing the mixture to stand at room temperature for 5 hours, water (5 ml) was added and the reaction solution was allowed to stand at room temperature for 30 minutes and was then concentrated. The concentrated solution was distributed between ethyl acetate (150 ml) and an aqueous solution of sodium bicarbonate (150 ml). The aqueous layer was extracted twice with ethyl acetate (each 150 ml). The extracts were combined with the ethyl acetate layer. The combined organic phase was washed with saturated sodium chloride solution and dried over magnesium sulfate. The residue was purified by silica gel column chromatography in hexane/ethyl acetate (10:1 to 5:1 v/v) to obtain Compound 14 (506 mg) as a colourless powder with a yield of 96%.

EXAMPLE 15

UCY1003 (50 mg) was dissolved in tetrahydrofuran (5 ml), and then 2N hydrochloric acid (1 ml) was added to the solution. The mixture was stirred at room temperature for 30 minutes. The reaction solution was neutralized with saturated aqueous sodium bicarbonate. The solvent was removed from the reaction solution by evaporation under reduced pressure Ethyl acetate (50 ml) and water (50 ml) were used to distribute the residue. The water layer was extracted twice with ethyl acetate (each 50 ml). The extracts were combined with the ethyl acetate layer. The combined organic phase was washed with saturated sodium chloride solution and dried over magnesium sulfate. After removal of the solvent from the reaction solution by evaporation under reduced pressure, the residue was purified by silica gel column chromatography using a solvent system of hexane/ethyl acetate (3:1 v/v) to obtain Compound 15 (52 mg) as a colourless powder with a yield of 96%.

EXAMPLE 16

Compound 9 (50 mg) was dissolved in acetic anhydride (0.5ml) and pyridine (1 ml) and allowed to stand at room temperature for one hour. After addition of water (0,5 ml), the reaction solution was further allowed to stand for 30 minutes. The solution was then evaporated under reduced pressure to remove the solvent. The residue was dissolved in acetone (2 ml) and the Jones reagent (0.2 ml) was added thereto. The mixture was stirred at room temperature for 30 minutes. The reaction solution was neutralized with saturated aqueous sodium bicarbonate while cooling with ice. Ethyl acetate (50 ml) and water (50 ml) were used to distribute the residue. The water layer was extracted twice with ethyl acetate (each 50 ml). The extracts were combined with the ethyl acetate layer. The combined organic phase was washed with a saturated solution of sodium chloride and dried by using magnesium sulfate.

After removal of the solvent from the reaction solution by evaporation under reduced pressure, the residue was purified by silica gel column chromatography using hexane/ethyl acetate (3:1 v/v) to obtain Copound 16 (45 mg) as a colourless powder with a yield of 83%.

We claim:

1. Compounds having the formula (I):

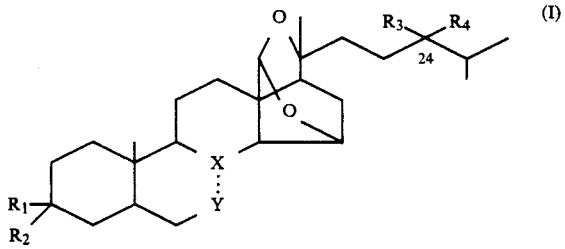

[wherein one of $R_1$ and $R_2$ represents hydrogen and the other represents OR (wherein R represents hydrogen or a $C_1$–$C_4$- alkanoyl group), or $R_1$ and $R_2$ in combination together represent a keto group; one of $R_3$ and $R_4$ represents hydrogen and the other represents methyl; or $R_3$ and $R_4$ in combination together represent $CH_2$:

X and ... Y - are combined together and represent

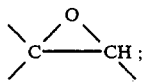

(wherein Z represents hydrogen or halo or

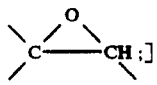

provided that when $R_1$ represents... H and $R_2$ represents - OH and when $R_3$ and $R_4$ in combination together represent $CH_2$, X ... Y are combined together and do not represent

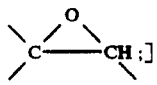;]

2. Compounds according to claim 1, wherein one of $R_1$ and $R_2$ represents hydroxyl or acetyloxy.

3. An analgesic composition comprising an effective amount pharmacologically acceptable carrier or excipient.

4. A method for the relief of pain which comprises the steps of administering an analgesic amount of a compound according to claim 1 to patients requiring analgesia.

5. A compound having the formula (II):

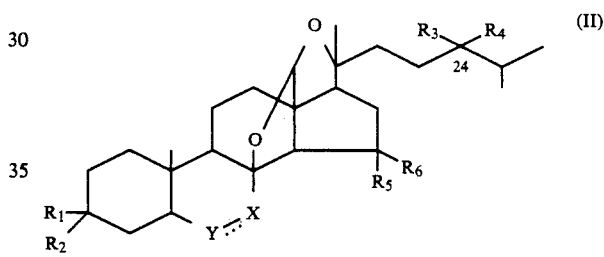

[wherein one of $R_1$ and $R_2$ represents hydrogen and the other represents OR (wherein R represents hydrogen atom or a $C_1$–$C_4$-(alkanoyl group)
or $R_1$ and $R_2$ in combination together represent a keto group;
one of $R_3$ and $R_4$ represents hydrogen and the other represents methyl; or $R_3$ and $R_4$ in combination together represent $CH_2$;
$R_5$ and $R_6$ each represents hydrogen or hydroxyl or $R_5$ and $R_6$ in combination together represent a keto group:
—X ... Y—represents —CHZ—$CH_2$—(wherein Z represents hydrogen or halogen) or —CH CH—].

6. Compounds according to claim 5 wherein one of $R_1$ and $R_2$ represents hydroxy or acetyloxy.

7. An analgesic composition comprising an effective amount of a compound according to claim 5 or claim 6 and a pharmaceutically acceptable carrier or excipient.

8. The compound according to claim 5 wherein one of $R_1$ and $R_2$ represents hydroxy or acetyloxy;
one of $R_3$ and $R_4$ represents methyl:
one of $R_5$ and $R_6$ represents hydroxy and the other represents hydrogen:
and Z represents bromine.

9. A method for the relief of pain which comprises the steps of administering an analgesic amount of a compound according to claim 5 to patients requiring analgesia.

* * * * *

UNITED STATES PATENT AND TRADEMARK OFFICE
CERTIFICATE OF CORRECTION

PATENT NO. : 4,952,576

DATED : August 28, 1990

INVENTOR(S) : Toru Yasuzawa, et al

Page 1 of 14

It is certified that error appears in the above-identified patent and that said Letters Patent is hereby corrected as shown below:

Columns 1 - 26 should be deleted to appear as per attached columns 1 - 26.

Signed and Sealed this

Nineteenth Day of January, 1993

Attest:

DOUGLAS B. COMER

Attesting Officer

Acting Commissioner of Patents and Trademarks

UCY1003 DERIVATIVES

The present invention relates to UCY1003 derivatives which exhibit analgesic activity.

It is known that certain steroid-type compound such as, for example, triamcinolone, methylprednisolone and dexamethasone have analgesic activity [Igaku no Ayumi (Development of Medical Science) 139 (1), 41 (1986)]. It is also known that the steroide substance designated UCY1003 has analgesic activity (EP-A-228 700).

Additional and/or improved analgesic agents are always needed. We have now prepared new UCY1003 derivatives having a surprising level of analgesic activity.

The present invention provides new UCY1003 derivatives having analgesic activity and represented by the formula:

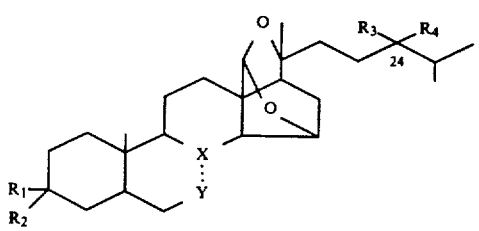

[wherein one of $R_1$ and $R_2$ represents hydrogen and the other represents OR (wherein R represents hydrogen or a $C_1$-$C_4$- alkanoyl group), or $R_1$ and $R_2$ in combination together represent a keto group; one of $R_3$ and $R_4$ represents hydrogen and the other represents methyl; or $R_3$ and $R_4$ in combination together represent $CH_2$: X and ...Y - are combined together and represent

(wherein Z represents hydrogen or halogen) or

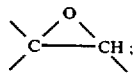

or X and ...Y - are not combined together and X represents C=O and Y represents COOH: provided that when $R_1$ represents ...H and $R_2$ represents -OH and when $R_3$ and $R_4$ in combination together represent $CH_2$, X ...Y are combined together and do not represent

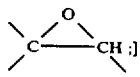

In another aspect, our invention provides UCY1003 derivatives represented by the formula (II):-

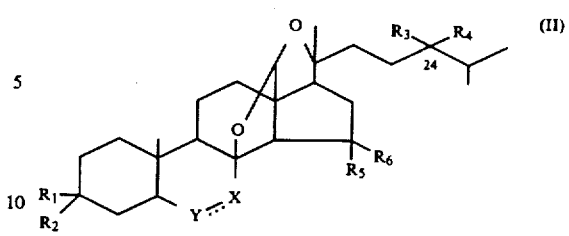

[wherein one of $R_1$ and $R_2$ represents hydrogen and the other represents OR (wherein R represents hydrogen atom or a $C_1$-$C_4$-(alkanoyl group)

or $R_1$ and $R_2$ in combination together represent a keto group;

one of $R_3$ and $R_4$ represents hydrogen and the other represents methyl; or $R_3$ and $R_4$ in combination together represent $CH_2$;

$R_5$ and $R_6$ each represents hydrogen or hydroxyl or $R_5$ and $R_6$ in combination together represent a keto group: —X=Y represents —CHZ—$CH_2$—(wherein Z represents hydrogen or halogen) or —CH=CH—].

In the above formulae, examples of suitable $C_1$-$C_4$ alkanoyl groups include straight or branched alkanoyl such as formyl, acetyl and propionyl groups; suitable halogen atoms are exemplified by chlorine and bromine.

Compounds of superior analgesic activity include those wherein one of $R_1$ and $R_2$ represents hydroxy or acetyloxy; Z presently represents chlorine or bromine. Compound of particular interest include those wherein one of $R_1$ and $R_2$ represents hydroxy or acetyloxyl;

one of $R_3$ and $R_4$ represents methyl:

one of $R_5$ and $R_6$ represents hydroxy and the other represents hydrogen:

and Z represents bromine.

For analgesic use, the compound may be formulated in conventional manner by admixing an effective amount with a pharmacologically acceptable carrier or excipient.

Suitable $C_1$-$C_4$ alkanoyl groups have already been described.

Step 1

Compound 1a may be obtained by the reaction of UCY1003 with a carboxylic acid anhydride or acyl halide in an aprotic organic solvent, in the presence of a base.

Suitable carboxylic acid anhydrides and acyl halides include, for example, anhydrides and acyl halides of acetic acid, propionic acid, lactic acid and isolactic acid. Such acid anhydrides and acyl halides may e.g. be used in a ratio of 5-20 moles per mole of UCY1003. Suitable aprotic organic solvents are exemplified by chloroform, dichloromethane, trichloroethane, benzene, toluene, acetone, ethyl acetate, trichloroethane, dioxane, tetrahydrofuran and dimethylformamide.

Suitable bases include tertiary amines and alkali metal carbonates, e.g. pyridine, quinoline, triethylamine, sodium carbonate and potassium carbonate. Especially good results may be obtained by the use of pyridine. An excess of pyridine may serve as the aprotic organic solvent.

The reaction may be effected at a temperature of −10° to 120° C., preferably 10° to 30° C. for a period of e.g. 0.5 to 20 hours preferably 3 to 8 hours.

The reaction product may be isolated by pouring the reaction solution into water. The product so isolated may have a sufficient purity for use or may, if desired, be purified further, for example, by column chromatography on silica gel or by recrystallization from an organic solvent.

Suitable organic solvents include, for example, chloroform, benzene, toluene, acetone, ethyl acetate, hexane, methanol, ethanol and ether, although the use of methanol or ethyl acetate is preferred.

Step 2

Compound 1b may be obtained by treating UCY1003 with an oxidizing agent derived from chromium (VI) oxide in an organic solvent.

Suitable oxidizing agents derived from chromium (VI) oxide are exemplified by chromium (VI) oxide-sulfuric acid (Jones reagent), chromium (VI) oxide-acetic acid, chromium (VI) oxide-pyridine complex (Collins reagent), pyridinium dichromate (PDC) reagent and pyridinium chlorochromate (PCC) reagent. The use of Jones reagent, PDC reagent or PCC reagent is preferred.

Preferably one uses from 3 to 5 moles of the oxidizing agent per mole of UCY1003.

Examples of suitable inert organic solvents include methylene dichloride, cis-1, 2-dichloroethylene, trans-1, 2-dichloroethylene, pyridine, chloroform, 1,2-dichloroethane, 1,1-dichloroethane, carbon tetrachloride, dimethyl sulfoxide and dimethylformamide. Especially good results may be obtained by using methylene dichloride.

The reaction may e.g. be effected at a temperature of from 0° to 40° C., preferably 10° to 25° C., for a period of e.g. 5 minutes to 24 hours, preferably 0.5 to 5 hours.

The purification in this step (and in the following steps) may be effected in a similar manner to that described in Step 1.

Step 3

Compound 1c may be prepared by catalytic hydrogenation of UCY1003 in an organic solvent.

Examples of suitable organic solvents include ethanol, methanol, tetrahydrofuran, ethyl acetate, dioxane, cyclohexane, acetic acid and dimethylformamide. Methanol is preferred. Suitable catalysts are e.g. based on nickel, platinum, rhodium or most preferably palladium.

The reaction may be effected at a temperature of e.g. −0° to 60° C., preferably 20° to 30° C. for a period of e.g. 0.5 to 10 hours, preferably 0.5 to 2 hours.

The product is usually a mixture of isomers having different absolute configurations at the 24th position in a molar ratio of from 1:4 to 4:1.

Step 4

Compound 1d may be obtained by treating UCY1003 with an oxidizing agent derived from chromium (VI) oxide in an inert organic solvent.

Examples of inert organic solvents include methylene dichloride, cis-1, 2-dichloroethylene, trans-1, 2-dichloroethylene, pyridine, chloroform, 1, 2-dichloroethane, 1, 1-dichloroethane, carbon tetrachloride, dimethylsulfoxide and dimethylformamide. Especially good results may be obtained by the use of methylene dichloride. Suitable oxidizing agents are exemplified by chromium (VI) oxide-sulfuric acid (Jones reagent).

One may use preferably from 3 to 5 moles of the oxidizing agent per mole of UCY1003.

The reaction may be effected at a temperature of e.g. 10° to 40° C., preferably 20° to 30° C., for a period of e.g. 0.5 to 24 hours, preferably 0.5 to 5 hours.

Step 5

Compound 1e (wherein Z=halogen) may be prepared by the raction of UCY1003 with a hydrohalic acid, e.g. hydrochloric or hydrobromic acid, in an organic solvent.

Examples of suitable organic solvents include ethanol, methanol, methylene dichloride, chloroform, ethyl acetate, acetone, tetrahydrofuran, dioxane, dimethylformamide and dimethylsulfoxide. Especially good results may be obtained by the use of tetrahydrofuran.

The reaction may e.g. be effected at a temperature of −20° to 50° C., preferably 0° to 30° C. for a period of 5 minutes to 5 hours, preferably from 10 minutes to one hour.

Compound 1e (wherein Z=H) may be prepared by treating UCY1003 with a reducing agent in an inert organic solvent.

Suitable solvents inert in this reaction are exemplified by ether, benzene, toluene, xylene, hexane, tetrahydrofuran, 1,2-dimethoxyethane and diglyme. The use of tetrahydrofuran is preferred.

Suitable reducing agents are exemplified by lithium aluminium hydride and its alkoxy derivatives containing, for example, methoxy, ethoxy, tert-butoxy or methoxyethoxy. We prefer to use lithium aluminium hydride.

The reaction may e.g. be effected at a temperature of from 0° to 100° C., preferably 40° to 70° C. for a period of from 1 minute to 10 hours, preferably from 10 minutes to 3 hours.

Step 6

Compound IIa may be obtained by allowing Compound Ia to stand in an organic solvent e.g. at a temperature of from 0° to 100° C., preferably 10° to 70° C. for a period of from 30 minutes to 3 days, preferably from 1 to 20 hours. If desired, the reaction may be accelerated by an catalytic acid, e.g. formic, acetic, para-toluenesulfonic, trifluoroacetic, hydrochloric, hydrobromic, sulfuric, nitric or phosphoric acid. The use of hydrochloric acid is preferred.

Suitable organic solvents include chloroform, dichloromethane, dichloroethane, benzene, toluene, aceton, ethyl acetate, dioxane, tetrahydrofuran, methanol and ethanol. The use of tetrahydrofuran is preferred.

Step 7

It is also possible to obtain Compound IIa in a similar manner to that described in Step 6 except the use of UCY1003 instead of Compound 1e.

Step 8

Compound IIc may be obtained by heating Compound IIa in an organic solvent containing a base e.g. at a temperature of from 20° to 200° C., preferably from 50° to 80° C. for a period of from 30 minutes to 20 hours, preferably from 1 to 10 hours.

Suitable organic solvents include methanol, ethanol, acetone, tetrahydrofuran, dioxane, 2-methoxyethanol, ethylene glycol, dimethylformamide and dimethylsulfoxide. These organic solvents may be used in anhydrous or aqueous form. We prefer to use methanol.

Suitable bases include sodium hydoxide, potassium hydroxide, lithium hydroxide, lithium carbonate, calcium carbonate, pyridine, collidine, sodium ethoxide, potassium tert-butoxide, 1.8-diazabicyclo (7,4,0) -7- undecene, 1,5-diazabicyclo [4.3.0] non-5-ene, and hexamethylphosphorotriamide. The use of potassium hydroxide is preferred.

Step 9

Compound IId may be obtained in a similar manner to that described in Step 1, starting from Compound IIa instead of UCY1003.

Step 10

Compound IIb may be obtained by treating Compound IId with an oxidizing agent derived from chromium (VI) oxide in an inert organic solvent. Suitable oxidizing agents and solvents are those defined for Step 2 above.

Preferably one may use from 3 to 5 moles of the oxidizing agent per mole of Compound IId.

The reaction may be effected e.g. at a temperature of from 0° to 80° C., preferably from 10° to 25° C. for a period of from 10 minutes to 20 hours, preferably from 0.5 to 5 hours.

Step 11

Compound IIe may be obtained from Compound Ic under the conditions described in Step 7.

The resultant product is usually a mixture of isomers having different absolute configurations at the 24th position, whose ratio corresponds to the isomer mixture in Compound Ic.

Step 12

Compound IIf may be obtained in a similar manner to that described in Step 1 except for the use of Compound IIe as starting material instead of UCY1003.

The product is usually a mixture of substances having different absolute configurations at the 24th position, thus corresponding to the isomer mixture in Compound IIe.

The following Table 1 indicates preferred examples of the compounds of the present invention and intermediate therefore wherein Compounds 1–16 correspond respectively to the compounds obtained in Examples 1–16 described hereinafter.

TABLE 1

| Compound No. | Formula |
| --- | --- |
| 1 | |
| 2 | |
| 3 | |
| 4 | |

TABLE 1-continued

| Compound No. | Formula |
|---|---|
| 5 | |
| 6 | |
| 7 | |
| 8 | |
| 9 | |
| 10 | |

TABLE 1-continued

| Compound No. | Formula |
|---|---|
| 11 | (structure) |
| 12 | (structure) |
| 13 | (structure) |
| 14 | (structure) |
| 15 | (structure) |
| 16 | (structure) |

The physico-chemical characteristics of Compounds 1–16 are shown in the following Tables 2 and 3.

Table 2 indicates the molecular formula, Rf by TLC, melting point and specific rotation of each compound. The following footnotes apply to Table 2:

(1) the molecular formula was determined from the elemental analysis or high resolution mass spectrometry:

(2) the Rf was determined by TLC using a solvent system of hexane/ethyl acetate (1:1 v/v):

(3) Rf was determined by TLC using a solvent system of chloroform/methanol/acetic acid (10:1:0.1 v/v);

(4) Rf was determined by TLC using a solvent system of hexane/ethyl acetate (5:1 v/v); and (5) all Rf values were determined by using TLC plate Kieselgel 60 F254 (commercial product of Merck AG., West Germany).

The physico-chemical characteritics of Compounds 1–16 are shown in the following Tables 2 and 3.

TABLE 2

| Compound No. | Molecular formula[1] | Rf by TLC[2,5] | M.P. (°C.) | $[\alpha]_D^{22}$ (CHCl$_3$) |
|---|---|---|---|---|
| 1 | $C_{30}H_{44}O_5$ | 0.61 | 238–239 | −62.5° |
| 2 | $C_{28}H_{40}O_4$ | 0.30 | 226–227 | −29.3° |
| 3 | $C_{28}H_{44}O_4$ | 0.13 | 234–235 | −55.3° |
| 4 | $C_{28}H_{40}O_6$ | 0.62[3] | 170–171 | −5.0° |
| 5 | $C_{28}H_{43}O_4Cl$ | 0.55 | 161–162 | −57.9° |
| 6 | $C_{28}H_{44}O_4$ | 0.45 | 206–207 | −25.6° |
| 7 | $C_{28}H_{43}O_4Cl$ | 0.54 | 169–170 | −43.7° |
| 8 | $C_{28}H_{43}O_4Br$ | 0.50 | 211–212 | −82.0° |
| 9 | $C_{28}H_{44}O_4$ | 0.33 | 171–172 | −9.3° |
| 10 | $C_{30}H_{43}O_5Cl$ | 0.80 | 216–217 | −53.4° |
| 11 | $C_{28}H_{42}O_4$ | 0.33 | 177–178 | −56.7° |
| 12 | $C_{30}H_{45}O_5Br$ | 0.43[4] | 161–162 | −80.1° |
| 13 | $C_{28}H_{45}O_4Br$ | 0.53 | 219–220 | −91.1° |
| 14 | $C_{30}H_{47}O_5Br$ | 0.45[4] | 179–180 | −64.7° |
| 15 | $C_{28}H_{43}O_4Cl$ | 0.61 | 171–172 | −50.8° |
| 16 | $C_{30}H_{44}O_5$ | 0.79 | 210–211 | +18.9° |

TABLE 3

Table 3 indicates carbon-NMR of each compound in deutrochloroform

| 1 | 2 | 3 | 4 | 5 | 6 | 7 | 8 |
|---|---|---|---|---|---|---|---|
| 170.7 | 210.6 | 106.6 | 210.5 | 155.4 | 155.6 | 155.3 | 155.1 |
| 155.6 | 155.5 | 85.6, 85.5 | 205.5 | 106.7 | 107.1 | 109.2 | 109.3 |
| 106.7 | 106.6 | 72.8 | 176.7 | 106.5 | 106.5 | 106.8 | 106.8 |
| 106.4 | 106.4 | 71.0 | 155.2 | 85.3 | 85.0 | 93.9 | 93.7 |
| 85.2 | 85.2 | 60.2 | 106.5 | 74.7 | 74.3 | 88.7 | 88.5 |
| 73.1 | 72.8 | 58.6 | 105.1 | 74.1 | 71.9 | 73.5 | 73.5 |
| 72.8 | 60.3 | 56.5 | 86.1 | 71.0 | 71.4 | 70.8 | 70.6 |
| 60.1 | 58.6 | 54.6 | 72.4 | 60.9 | 61.6 | 63.5(2) | 64.4 |
| 58.7 | 56.1 | 49.0, 48.9 | 64.3 | 58.0 | 57.3 | | 63.8 |
| 56.4 | 54.3 | 48.7 | 63.5 | 57.7 | 53.8 | 60.6 | 54.7 |
| 54.5 | 49.0 | 39.8 | 55.2 | 49.2 | 49.2 | 52.6 | 52.5 |
| 49.1 | 48.0 | 39.4, 39.2 | 49.2 | 47.2 | 45.4 | 48.2 | 48.0 |
| 48.6 | 43.9 | 39.2, 39.1 | 42.6 | 39.5 | 40.3 | 38.1 | 37.9(2) |
| 39.6(2) | 42.0 | 38.1 | 39.5 | 38.1 | 39.6 | 37.5 | |
| | 39.6 | 37.4 | 39.1 | 37.6 | 37.8 | 37.0 | 37.4 |
| 37.8 | 39.4 | 35.5, 35.4 | 37.2 | 36.8 | 37.5 | 36.9 | 36.8(2) |
| 35.4 | 37.3 | 33.9 | 36.5 | 36.0 | 35.8 | 36.7 | |
| 33.9(2) | 35.3 | 31.9, 31.8 | 35.0 | 34.9 | 35.2 | 36.5 | 36.6 |
| | 34.0 | 30.8 | 34.0 | 34.0 | 34.0 | 33.9 | 34.5 |
| 33.3 | 33.9 | 29.2, 28.9 | 33.8 | 33.7 | 31.0 | 33.7 | 33.8 |
| 29.5 | 29.4 | 28.6 | 30.3 | 30.7 | 29.5 | 32.4 | 32.3 |
| 28.4 | 28.9 | 28.4 | 29.2 | 29.4 | 28.8 | 30.5 | 30.4 |
| 28.3 | 28.2 | 27.4 | 27.5 | 28.1 | 24.9 | 28.3 | 28.2 |
| 27.4 | 27.4 | 21.7 | 27.1 | 27.2 | 27.2 | 24.9 | 24.8 |
| 26.7 | 21.9(2) | 20.4, 20.2 | 25.4 | 21.9(2) | 21.9(2) | 21.9(2) | 21.8(2) |
| 21.9(2) | | 18.2, 17.7 | 21.8(2) | | | | |
| | 21.8 | 15.5, 15.3 | | 19.0 | 18.9 | 20.6 | 20.5 |
| 21.7 | 12.0 | 12.8 | 16.7 | 12.7 | 12.5 | 12.1 | 12.2 |
| 21.4 | | | | | | | |
| 12.7 | | | | | | | |

| 9 | 10 | 11 | 12 | 13 | 14 | 15 | 16 |
|---|---|---|---|---|---|---|---|
| 155.5 | 207.3 | 155.4 | 170.5 | 109.4 | 170.6 | 155.4 | 210.2 |
| 108.3 | 170.6 | 135.0 | 155.3 | 93.7 | 109.4 | 106.9 | 170.7 |
| 106.7 | 155.0 | 126.4 | 109.4 | 89.2 | 93.7 | 106.6 | 155.2 |
| 91.8 | 108.8 | 107.7 | 106.9 | 73.7 | 89.2 | 85.3 | 108.0 |
| 88.1 | 106.7 | 106.7 | 93.8 | 70.9 | 73.7 | 75.0 | 106.6 |
| 73.1 | 92.3 | 89.2 | 88.7 | 64.6 | 73.1 | 74.2 | 90.7 |
| 71.1 | 88.3 | 88.2 | 73.7 | 63.9 | 64.6 | 71.0 | 87.5 |
| 64.4 | 73.0 | 72.9 | 73.0 | 54.9 | 63.9 | 65.3 | 73.3 |
| 64.1 | 60.7 | 71.4 | 64.5 | 52.7, 52.5 | 54.4 | 57.6 | 62.8 |
| 54.7 | 59.5 | 65.5 | 63.9 | 48.2 | 52.7, 52.5 | 56.3 | 60.2 |
| 52.5 | 59.3 | 64.4 | 54.3 | 39.2, 39.0 | 48.0 | 49.2 | 54.5 |
| 44.8 | 47.2 | 55.1 | 52.8 | 38.1(2) | 39.2, 39.0 | 47.3 | 45.4 |
| 38.6 | 45.0 | 52.3 | 48.0 | | 38.1 | 39.5 | 44.5 |
| 38.0 | 41.0 | 45.2 | 38.0 | 37.6 | 37.9 | 37.6 | 41.4 |
| 37.8 | 37.1 | 38.5 | 37.9 | 37.0 | 37.3 | 36.9 | 37.5 |
| 36.9 | 36.9(2) | 36.9 | 37.2 | 36.8 | 36.7 | 36.8 | 36.5 |
| 36.3 | | 36.2 | 37.0 | 36.3, 36.1 | 36.3, 36.1 | 35.9 | 36.3 |
| 33.9 | 36.3 | 35.1 | 36.7 | 34.6 | 34.5 | 34.9 | 34.0 |
| 32.7 | 34.1 | 34.5 | 34.4 | 32.4 | 32.9 | 34.0 | 33.7 |
| 31.8 | 33.2 | 33.9 | 34.0 | 32.0 | 32.4 | 33.0 | 32.8 |
| 30.8 | 32.8 | 32.6 | 32.9 | 30.6 | 32.0 | 30.8 | 31.7 |
| 28.4 | 32.5 | 30.7 | 32.4 | 28.1, 27.8 | 28.0, 27.8 | 29.4 | 28.3 |
| 25.5 | 28.2 | 28.3 | 28.4 | 24.9 | 26.7 | 28.2 | 26.7 |

TABLE 3-continued

Table 3 indicates carbon-NMR of each compound in deutrochloroform

| | | | | | | | | | |
|---|---|---|---|---|---|---|---|---|---|
| 24.9 | 26.6 | 24.7 | 26.6 | 20.7 | | 24.9 | | 27.2 | 25.1 |
| 21.9(2) | 24.3 | 21.9(2) | 24.9 | 20.4, | 20.3 | 21.4 | | 21.9(2) | 24.2 |
| | 21.9(2) | | 21.9(2) | 18.2, | 17.9 | 20.6 | | 18.9 | 21.94 |
| 21.0 | | 21.1 | | 15.4 | | 20.35, | 20.26 | 12.6 | 21.89 |
| 12.1 | 21.4 | 11.1 | 21.4 | 12.4 | | 18.2, 17.9 | | | 21.4 |
| | 20.5 | | 20.6 | | | 15.4 | | | 20.9 |
| | 11.9 | | 12.2 | | | 12.3 | | | 12.0 |

Ppm was determined by using tetramethylsilane as the internal standard.

Acute toxicities and analgesic activities of the compounds of the present invention are as follows:

1. Acute toxicity:

3 mice of ddy strain were used as test animals. After intraperitioneal administration of test compounds, the animals were observed for 7 days to note the death ratio.

It was found that zero mortality resulted from administration of the compounds at a dose of 300 mg/kg.

2. Analgesic effect:

As test animals, female mice of ddy strain (body weight 20±1 g; each group consisting of 4 mice) were used. Each test compound was administered intraperitioneally. 60 minutes later, 0.7 % acetic acid solution (0.2 ml) was intraperitioneally administered and the number of writhing movements made within a period of 10 to 15 minutes after administration was noted. Where the number of writhing movements decreased by more than 70% relative to the control (untreated) animals, it was concluded that the analgesic effect was positive.

The minimum effective doses (MED) thus obtained are shown in Table 4.

TABLE 4

| Compound No. | MED (mg/kg) |
|---|---|
| 1 | 10 |
| 2 | 10 |
| 3 | 5 |
| 4 | ≦100 |
| 5 | 25 |
| 6 | 10 |
| 7 | 100 |
| 8 | 2.5 |
| 9 | 25 |
| 10 | 10 |
| 11 | 25 |
| 12 | 5 |
| 13 | 0.25 |
| 14 | 1 |
| UCY 1003 | 50 |

The compounds of the present invention may be prepared as indicated below:

STEPS
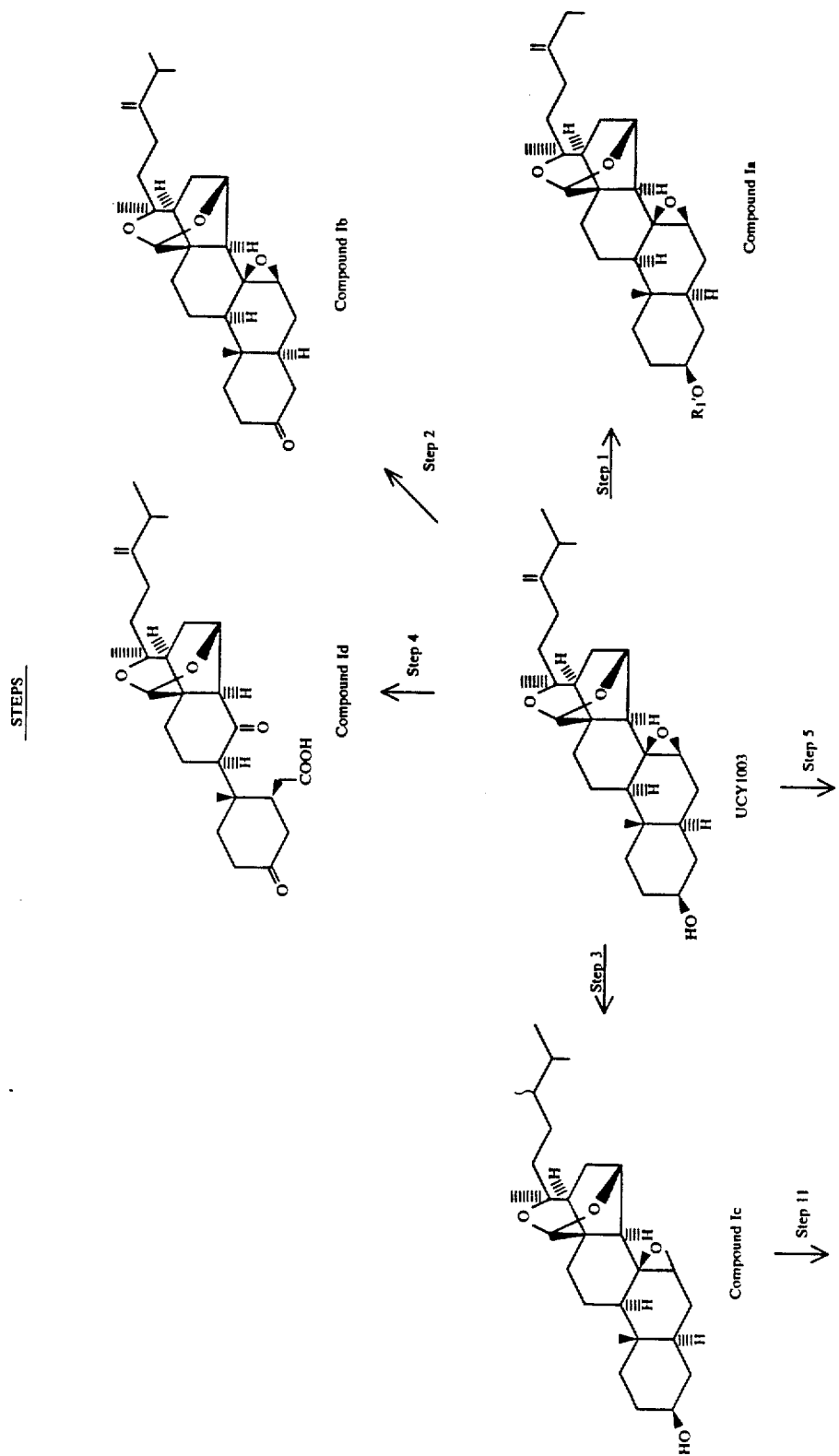

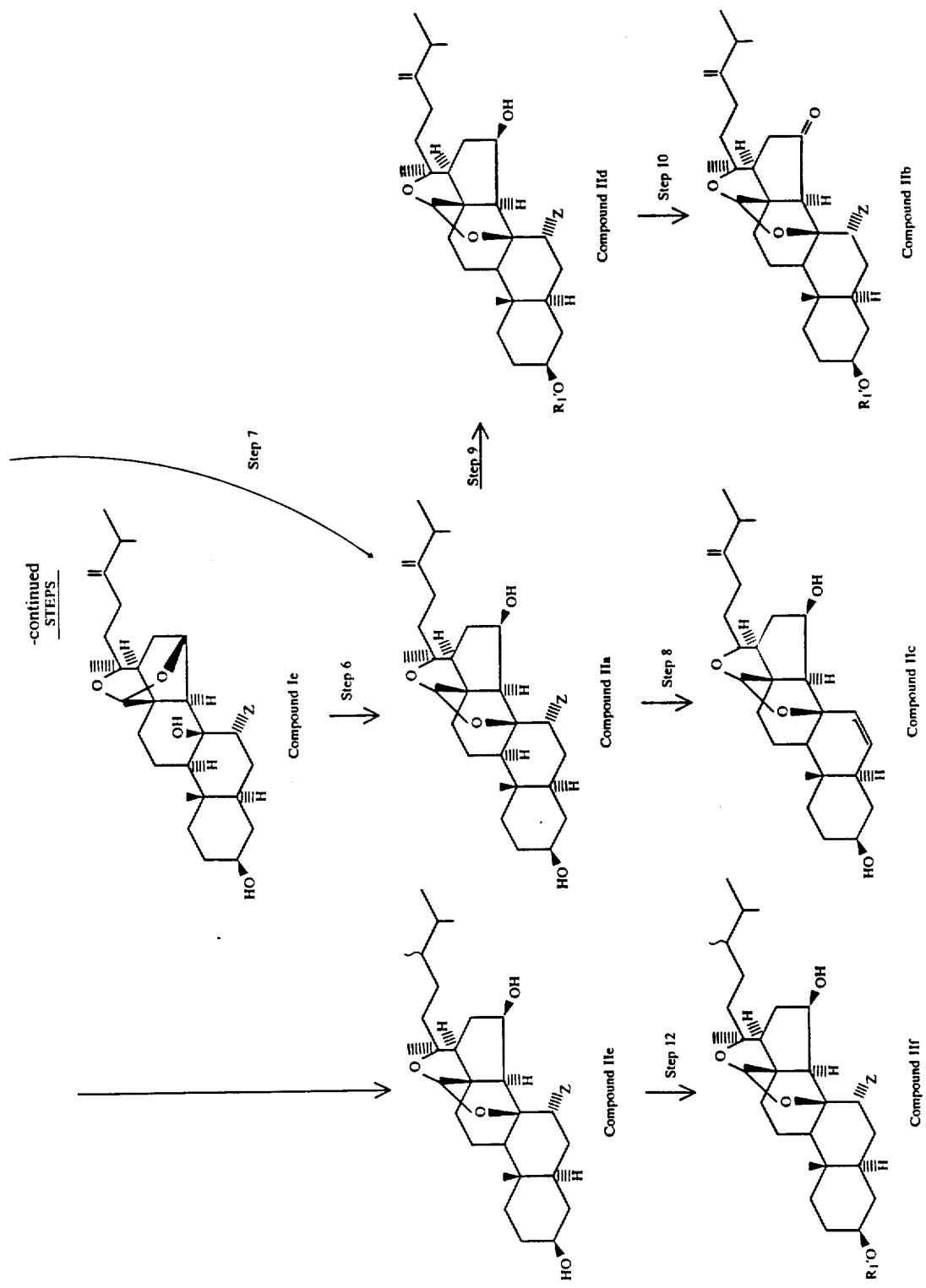

The following non-limiting Examples are given for illustration only.

UCY1003 used in the following Examples was obtained by the method of Example 1 of EP-A-228, 700.

EXAMPLE 1

UCY1003 (590 mg) was dissolved in pyridine (5 ml), and acetic anhydride (2 ml) was added thereto. After allowing the mixture to stand at room temperature for 5 hours, water (20 ml) was added. The solution was allowed to stand at room temperature for 30 minutes and then filtered to collect the precipitate. The precipitate was washed with water (100 ml) and dried at 80° C. for 3 hours to obtain Compound 1 (620 mg) as a colourless powder with a yield of 96%.

EXAMPLE 2

UCY1003 (802 mg) was dissolved in methylene chloride (20 ml). Pyridinium chlorochromate (PCC) reagent (1.61 g) was added to the solution, followed by stirring at room temperature for 2 hours. The reaction mixture was distributed between ethyl acetate (100 ml) and saturated aqueous sodium bicarbonate (100 ml). Then the aqueous layer was extracted twice with ethyl acetate (each 100 ml). The extracts were combined with the ethyl acetate layer. The combined organic fraction was washed with saturated sodium chloride solution (150 ml), dried over magnesium sulfate, and the solvent removed from by evaporation under reduced pressure to give a colourless powder. The powder was purified by silica gel column chromatography using a solvent system of hexane/ethyl acetate (1:2 v/v) to obtain Compound 2 (399 mg) as a colourless powder with a yield of 50%.

EXAMPLE 3

Palladium-carbon catalyst containing 10% palladium (450 mg) was stirred in methanol (30 ml) for 30 minutes under a hydrogen stream (1 atm). UCY1003 (620 mg), dissolved in methanol (20 ml), was added and the solution was stirred for 2 hours under the hydrogen stream. The reaction solution was filtered, the catalyst was washed with hot methanol (30 ml), and the combined filtrate and washing solution was evaporated under reduced pressure to give a colourless powder. The powder was purified by silica gel chromatography in chloroform/methanol (10:1 v/v) to obtain Compound 3 (440 mg) as a colourless powder, yield 71%.

EXAMPLE 4

UCY1003 (60 mg) was dissolved in acetone (5 ml). To this solution was added Jones reagent [0.2 ml; prepared from chromium trioxide (13.4 g), concentrated sulfuric acid (12 ml) and acetone (46 ml)]. The solution was stirred at room temperature for one hour and concetrated, then the mixture was distributed between ethyl acetate (30 ml) and water (30 ml). The water layer was extracted twice with ethyl acetate (each 30 ml) and the extracts were combined with the ethyl acetate layer. The combined organic fraction was washed with saturated sodium chloride solution and dried over magnesium sulfate. The residue was purified on silica gel column chromatography in chloroform/methanol/acetic acid (30:1:0.1 v/v) to obtain Compound 4 (33 mg) as a colourless powder with a yield of 52%.

EXAMPLE 5

UCY1003 (1.39 g) was dissolved in tetrahydrofuran (25 ml) and 2N hydrobromic acid solution (1.5 ml) was added. The mixture was stirred at room temperature for 20 minutes. The reaction solution was neutralized with saturated sodium bicarbonate solution, followed by removal of the solvent under reduced pressure. The residue was distributed between ethyl acetate (100 ml) and water (100 ml). The water layer was extracted twice with ethyl acetate (each 100 ml) and the extracts were combined with the ethyl acetate layer. The combined organic fraction was washed with saturated sodium chloride solution, dried over magnesium sulfate and the residue purified by silica gel column chromatography in hexane/ethyl acetate (2:1 v/v) to obtain Compound 5 (1.41 g) as a colourless powder with a yield of 86%.

EXAMPLE 6

UCY1003 (1.23 g) was dissolved in anhydrous tetrahydrofuran (50 ml), followed by addition of lithium aluminium hydride (250 mg). The mixture was refluxed for 30 minutes and allowed to cool. Ethyl acetate (5 ml), methanol (5 ml) and water (1 ml) were in turn added to the reaction solution, followed by stirring for 10 minutes. The solvent was removed from the solution by evaporation under reduced pressure to give a residue. The residue was then distributed between 0,1N hydrochloric acid (100 ml) and ethyl acetate (100 ml). The aqueous layer was extracted twice with ethyl acetate (each 100 ml) and the extracts were combined with the ethyl acetate layer. The combined organic phase was washed with saturated sodium bicarbonate solution (100 ml) and saturated sodium chloride solution (100 ml) and then dried over magnesium sulfate. The solvent was removed by evaporation under reduced pressure to obtain Compound 6 (1.21 g) as a colourless powder with a yield of 99%.

EXAMPLE 7

UCY1003 (302 mg) was dissolved in tetrahydrofuran (7 ml). 2N hydrochloric acid (0.5 ml) was added to the mixture, followed by stirring at room temperature for one hour. The reaction solution was then neutralized with saturated sodium bicarbonate solution. The reaction solution was evaporated under reduced pressure to remove the solvent and the residue was distributed between chloroform (50 ml) and water (50 ml). The aqueous layer was extracted twice with chloroform (each 50 ml), and the extracts were combined with the chloroform layer. The combined organic phase was washed with saturated sodium chloride solution and dried over magnesium sulfate. The resultant solution was evaporated under reduced pressure to remove the solvent. The residue was purified by silica gel column chromatogrpahy in hexane/ethyl acetate (2:1 v/v) to obtan Compound 7 (235 mg) as a colourless powder with a yield of 72%.

EXAMPLE 8

UCY1003 (750 mg) was dissolved in tetrahydrofuran (25 ml), to which was then added 2N hydrobromic acid (1.5 ml). The mixture was stirred at a temperature of 50° C. for 3 hours. The reaction solution was neutralized with saturated aqueous sodium bicarbonate and the solution was evaporated under reduced pressure to remove the solvent. Then the residue was distributed between ethyl acetate (100 ml) and water (100 ml). The aqueous layer was extracted twice with ethyl acetate (each 100 ml) and the extracts were combined with the ethyl acetate layer. The combined organic phase was washed with saturated sodium chloride solution and dried over magnesium sulfate. After removal of the solvent by evaporation under reduced pressure, the residue was purified by silica gel column chromatography in hexane/ethyl acetate (2;1 v/v) to obtain Compound 8 (620 mg) as a colourless powder with a yield of 70%.

EXAMPLE 9

Compound 6 (613 mg) was dissolved in tetrahydrofuran (50 ml) and 2N hydrochloric acid (2 ml) was added and the mixture was refluxed for 2 hours. The reaction solution was neutralized with saturated aqeuous sodium bicarbonate, the solvent was removed by evaporation under reduced pressure, and the residue was distributed between chloroform (50 ml) and water (50 ml). The aqueous layer was extracted twice with chloroform (each 50 ml). The extracts were combined with the chloroform layer and the combined organic phase was washed with saturated sodium bicarbonate solution (50 ml) and saturated sodium chloride solution (50 ml) and dried over magnesium sulfate.

After removal of the solvent by evaporation under reduced pressure, the residue was purified by silica gel column chromatography in hexane/ethyl acetate (1:1 v/v) to obtain Compound 9 (415 mg) as a colourless powder with a yield of 71%.

EXAMPLE 10

Compound 7 (6 mg) was dissolved in acetic anhydride (0.5 ml) and pyridine (1 ml) and allowed to stand at room temperature for one hour. After addition of water (0.5 ml), the mixture was allowed to stand for 30 minutes. The solvent was removed from the reaction solution by evaporation under redued pressure. The residue was dissolved in methylene chloride (1 ml). After addition of pyridinium chlorochromate (PCC) reagent (30 mg), the reaction solution was stirred at room temperature for 15 hours. The reaction mixture was distributed between ethyl acetate (30 ml) and water (30 ml). The water layer was extracted twice with ethyl acetate (each 30 ml). The extracts were combined with the ethyl acetate layer. After washing with saturated sodium chloride solution (30 ml), the combined organic phase was dried over magnesium sulfate.

After removal of the solvent by evaporation under reduced pressure, the residue was purified by silica gel column chromatography in hexane/ethyl acetate (5:1 v/v) to obtain Compound 10 (2.5 mg) as a colourless powder with a yield of 34%.

EXAMPLE 11

Compound 8 (275 mg) was dissolved in methanol (30 ml) and potassium hydroxide (5 g) was added to the solution. The mixture was refluxed for 5 hours. After the reaction mixture was concentrated, the concentrate was distributed between ethyl acetate (50 ml) and water (50 ml). The aqueous layer was extracted twice with ethyl acetate (each 30 ml). The extracts were combined with the ethyl acetate layer. The combined organic phase was washed with saturated sodium chloride solution and dried over magnesium sulfate. The residue was purified by silica gel column chromatography in hexane/ethyl acetate (2:1 v/v) to obtain Compound 11 (215 mg) as a colourless powder with a yield of 93%.

EXAMPLE 12

Compound 8 (607 mg) was dissolved in pyridine (10 ml) and acetic anhydride (3 ml) was added to the solution. The mixture was allowed to stand at room temperature for 5 hours. After addition of water (5 ml), the mixture was allowed to stand at room temperature for 30 minutes. The reaction solution was concentrated and distributed between ethyl acetate (150 ml) and aqueous sodium bicarbonate (150 ml). The aqueous layer was extracted twice with ethyl acetate (each 150 ml). The extracts were combined with the ethyl acetate layer. The combined organic phase was washed with saturated sodium chloride solution and dried over magnesium sulfate. The residue was purified by silica gel column chromatography in hexane/ethyl acetate (2:1 v/v) to obtain Compound 12 (590 mg) as a colourless powder with a yield of 90%.

EXAMPLE 13

Compound 3 (1.181 g) was dissolved in tetrahydrofuran (75 ml) and then 2N hydrobromic acid (1 ml) was added to the solution. The mixture was stirred at room temperature for 45 minutes. The reaction solution was neutralized with a saturated solution of sodium bicarbonate. The solvent was removed from the reaction solution by evaporation under reduced pressure. Ethyl acetate (150 ml) and water (150 ml) were used to distribute the residue. The aqueous layer was extracted twice with ethyl acetate (each 150 ml). The extract was combined with the ethyl acetate layer. The combined organic phase was washed with saturated sodium chloride solution and dried over magnesium sulfate. After removal of the solvent from the reaction solution by evaporation under reduced pressure, the residue (1.250 g) was dissolved in chloroform (30 ml). After addition of para-toluenesulfonic acid (200 mg), the solution was allowed to stand at room ternperature for 4 hours. Chloroform (150 ml) and aqueous sodium bicarbonate (150 ml) were used to distribute the reaction solution.

The water layer was extracted twice with chloroform (each 150 ml). The extracts were combined with the chloroform layer. The combined organic phase was washed with saturated solution of sodium chloride and dried over magnesium sulfate. After removal of the solvent by evaporation under reduced pressure, residue was purified by silica gel column chromatography in hexane/ethyl acetate (3:1 v/v) to obtain Compound 13 (1.008 g) as a colourless powder with a yield of 74%.

EXAMPLE 14

Compound 13 (489 mg) was dissolved in pyridine (10 ml). Acetic anhydride (2.5 ml) was added to the solution. After allowing the mixture to stand at room temperature for 5 hours, water (5 ml) was added and the reaction solution was allowed to stand at room temperature for 30 minutes and was then concentrated. The concentrated solution was distributed between ethyl acetate (150 ml) and an aqueous solution of sodium bicarbonate (150 ml). The aqueous layer was extracted twice with ethyl acetate (each 150 ml). The extracts were combined with the ethyl acetate layer. The combined organic phase was washed with saturated sodium chloride solution and dried over magnesium sulfate. The residue was purified by silica gel column chromatography in hexane/ethyl acetate (10:1 to 5:1 v/v) to obtain Compound 14 (506 mg) as a colourless powder with a yield of 96%.

EXAMPLE 15

UCY1003 (50 mg) was dissolved in tetrahydrofuran (5 ml), and then 2N hydrochloric acid (1 ml) was added to the solution. The mixture was stirred at room temperature for 30 minutes. The reaction solution was neutralized with saturated aqueous sodium bicarbonate. The solvent was removed from the reaction solution by evaporation under reduced pressure. Ethyl acetate (50 ml) and water (50 ml) were used to distribute the residue. The water layer was extracted twice with ethyl acetate (each 50 ml). The extracts were combined with the ethyl acetate layer. The combined organic phase was washed with saturated sodium chloride solution and dried over magnesium sulfate. After removal of the solvent from the reaction solution by evaporation under reduced pressure, the residue was purified by silica gel column chromatography using a solvent system of hexane/ethyl acetate (3:1 v/v) to obtain Compound 15 (52 mg) as a colourless powder with a yield of 96%.

EXAMPLE 16

Compound 9 (50 mg) was dissolved in acetic anhydride (0.5ml) and pyridine (1 ml) and allowed to stand at room temperature for one hour. After addition of water (0,5 ml), the reaction solution was further allowed to stand for 30 minutes. The solution was then evaporated under reduced pressure to remove the solvent. The residue was dissolved in acetone (2 ml) and the Jones reagent (0.2 ml) was added thereto. The mixture was stirred at room temperature for 30 minutes. The reaction solution was neutralized with saturated aqueous sodium bicarbonate while cooling with ice. Ethyl acetate (50 ml) and water (50 ml) were used to distribute the residue. The water layer was extracted twice with ethyl acetate (each 50 ml). The extracts were combined with the ethyl acetate layer. The combined organic phase was washed with a saturated solution of sodium chloride and dried by using magnesium sulfate.

After removal of the solvent from the reaction solution by evaporation under reduced pressure, the residue was purified by silica gel column chromatography using hexane/ethyl acetate (3:1 v/v) to obtain Copound 16 (45 mg) as a colourless powder with a yield of 83%.

We claim:

1. Compounds having the formula (I):

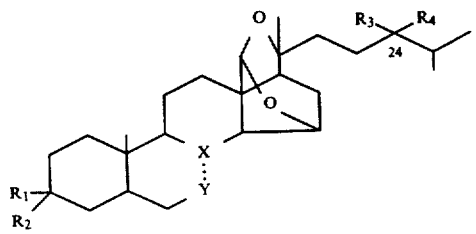

[wherein one of $R_1$ and $R_2$ represents hydrogen and the other represents OR (wherein R represents hydrogen or a $C_1$- $C_4$- alkanoyl group), or $R_1$ and $R_2$ in combination together represent a keto group; one of $R_3$ and $R_4$ represents hydrogen and the other represents methyl; or $R_3$ and $R_4$ in combination together represent $CH_2$:

X and ...Y - are combined together and represent

(wherein Z represents hydrogen or halogen) or

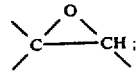

provided that when $R_1$ represents ...H and $R_2$ represents - OH and when $R_3$ and $R_4$ in combination together represent $CH_2$, X ...Y are combined together and do not represent

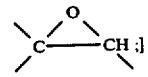

2. Compounds according to claim 1, wherein one of $R_1$ and $R_2$ represents hydroxyl or acetyloxy.

3. An analgesic composition comprising an effective amount of a compound according to claim 1 or claim 2 and a pharmacologically acceptable carrier or excipient.

4. A method for the relief of pain which comprises the steps of administering an analgesic amount of a compound according to claim 1 to patients requiring analgesia.

5. A compound having the formula (II):

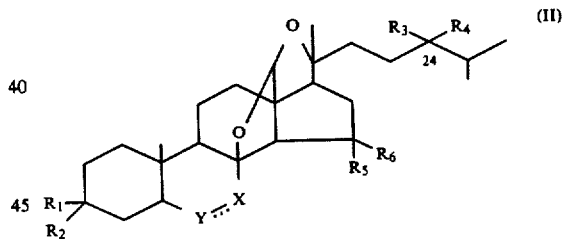

[wherein one of $R_1$ and $R_2$ represents hydrogen and the other represents OR (wherein R represents hydrogen atom or a $C_1$- $C_4$-(alkanoyl group)
or $R_1$ and $R_2$ in combination together represent a keto group;
one of $R_3$ and $R_4$ represents hydrogen and the other represents methyl; or $R_3$ and $R_4$ in combination together represent $CH_2$;
$R_5$ and $R_6$ each represents hydrogen or hydroxyl or $R_5$ and $R_6$ in combination together represent a keto group:
—X. ...Y - represents —CHZ—$CH_2$—(wherein Z represents hydrogen or halogen) or —CH=CH—].

6. Compounds according to claim 5 wherein one of $R_1$ and $R_2$ represents hydroxy or acetyloxy.

7. An analgesic composition comprising an effective amount of a compound according to claim 5 or claim 6 and a pharmacologically acceptable carrier or excipient.

8. The compound according to claim 5 wherein one of $R_1$ and $R_2$ represents hydroxy or acetyloxy; one of $R_3$ and $R_4$ represents methyl; one of $R_5$ and $R_6$ represents hydroxy and the other represents hydrogen; and Z represents bromine.

9. A method for the relief of pain which comprises the steps of administering an analgesic amount of a compound according to claim 5 to patients requiring analgesia.

* * * * *